(12) United States Patent
Kawano et al.

(10) Patent No.: US 10,539,701 B2
(45) Date of Patent: Jan. 21, 2020

(54) MINUTE MAGNETIC BODY DETECTING SENSOR AND FOREIGN SUBSTANCE DETECTING DEVICE

(71) Applicant: AICHI STEEL CORPORATION, Tokai-shi (JP)

(72) Inventors: Takeshi Kawano, Tokai (JP); Hideo Arakawa, Tokai (JP); Michiharu Yamamoto, Tokai (JP); Hitoshi Aoyama, Tokai (JP); Kazuo Urakawa, Tokai (JP)

(73) Assignee: AICHI STEEL CORPORATION, Tokai-shi (JP)

( * ) Notice: Subject to any disclaimer, the term of this patent is extended or adjusted under 35 U.S.C. 154(b) by 32 days.

(21) Appl. No.: 15/766,046

(22) PCT Filed: Oct. 5, 2016

(86) PCT No.: PCT/JP2016/079703
§ 371 (c)(1),
(2) Date: Apr. 5, 2018

(87) PCT Pub. No.: WO2017/061513
PCT Pub. Date: Apr. 13, 2017

(65) Prior Publication Data
US 2018/0284310 A1 Oct. 4, 2018

(30) Foreign Application Priority Data
Oct. 6, 2015 (JP) .................................. 2015-198967

(51) Int. Cl.
*G01V 3/08* (2006.01)
*G01R 33/04* (2006.01)
(Continued)

(52) U.S. Cl.
CPC ............. *G01V 3/081* (2013.01); *G01N 27/72* (2013.01); *G01R 33/02* (2013.01); *G01R 33/04* (2013.01); *G01V 3/08* (2013.01)

(58) Field of Classification Search
None
See application file for complete search history.

(56) References Cited

U.S. PATENT DOCUMENTS

| | | | | | |
|---|---|---|---|---|---|
| 5,757,184 | A | * | 5/1998 | Kurihara | ............... G01R 33/02 324/244 |
| 2003/0155913 | A1 | * | 8/2003 | Honkura | ............... G01R 33/02 324/249 |

(Continued)

FOREIGN PATENT DOCUMENTS

| | | |
|---|---|---|
| JP | 9-211144 A | 8/1997 |
| JP | 11-64474 A | 3/1999 |

(Continued)

OTHER PUBLICATIONS

International Search Report dated Dec. 20, 2016 in PCT/JP2016/079703, filed on Oct. 5, 2016.

(Continued)

*Primary Examiner* — Clayton E. LaBalle
*Assistant Examiner* — Jas A Sanghera
(74) *Attorney, Agent, or Firm* — Oblon, McClelland, Maier & Neustadt, L.L.P.

(57) ABSTRACT

A minute magnetic body detecting sensor includes: a magnetic impedance element, with two magneto-sensitive bodies disposed in substantially two-dimensional directions such that an angle formed by respective sensitive axes is substantially 90 degrees; and a signal processing device, including a signal processing circuit, processing and amplifying damped oscillating voltages output by the two magneto-sensitive bodies that detected a local magnetic field due to a minute magnetic body that is a foreign substance, two (Continued)

square operating elements, squaring output signals, an adder, adding the squared signals, and a square root operating element, performing square root computation on the addition output and outputting a square root output, and enables high-precision detection of existence or non-existence of a minute magnetic body without detection overlooking.

9 Claims, 22 Drawing Sheets

(51) Int. Cl.
*G01R 33/02* (2006.01)
*G01N 27/72* (2006.01)

(56) References Cited

U.S. PATENT DOCUMENTS

| | | |
|---|---|---|
| 2003/0164765 A1 | 9/2003 | Sumi et al. |
| 2005/0242805 A1* | 11/2005 | Honkura ............... G01R 33/02 324/249 |
| 2013/0181705 A1* | 7/2013 | Honkura ............. G01R 33/063 324/252 |
| 2015/0145509 A1* | 5/2015 | Takenaka ........... G01N 27/9046 324/207.21 |

FOREIGN PATENT DOCUMENTS

| | | |
|---|---|---|
| JP | 11-248851 A | 9/1999 |
| JP | 2005-283271 A | 10/2005 |
| JP | 2006-329963 A | 12/2006 |
| JP | 2007-113993 A | 5/2007 |
| JP | 2012-159292 A | 8/2012 |
| JP | 2015-10902 A | 1/2015 |
| JP | 2015-124999 A | 7/2015 |
| JP | 2015-175639 A | 10/2015 |
| KR | 10-2010-0121190 A | 11/2010 |
| WO | WO 2011/016302 A1 | 2/2011 |
| WO | 2011/155527 A1 | 12/2011 |
| WO | 2014/079740 A2 | 5/2014 |

OTHER PUBLICATIONS

Extended European Search Report dated May 15, 2019, in Patent Application No. 16853667.0, citing documents AA, and AO-AP therein, 16 pages.

* cited by examiner

Fig. 1
(a)
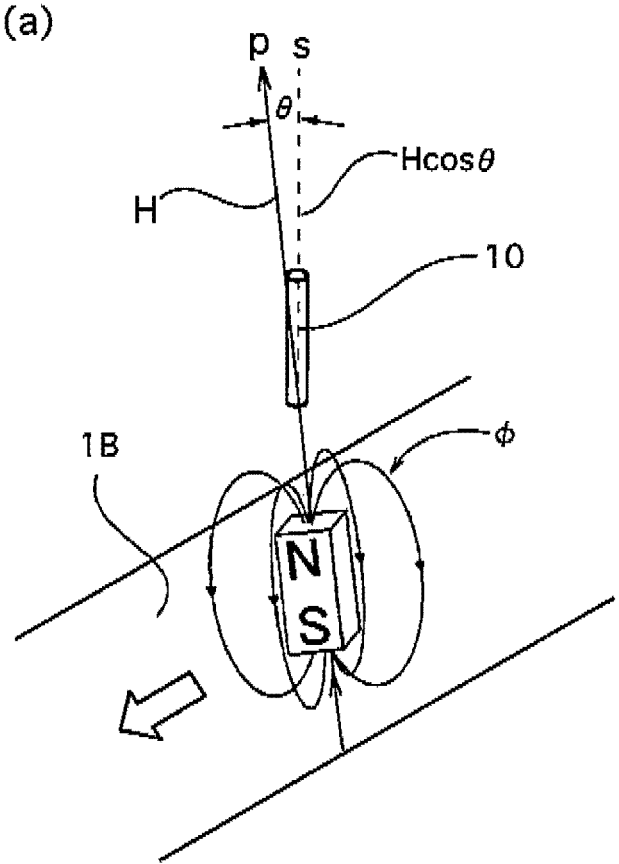
(b)
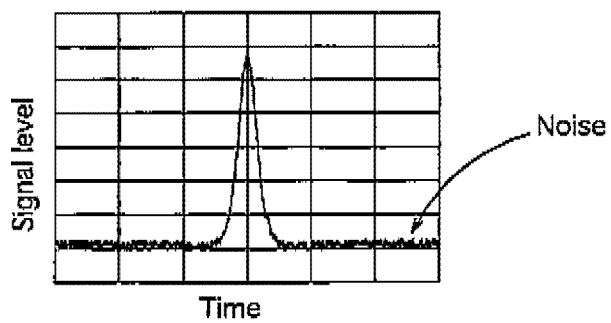

Fig. 2
(a)
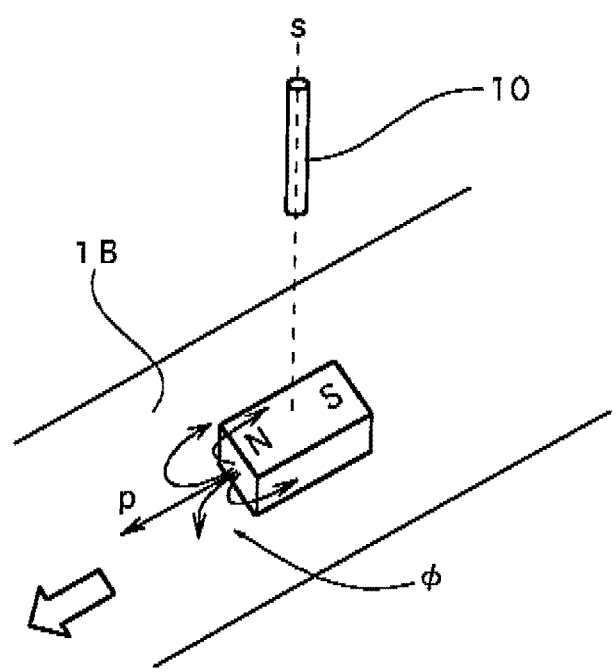
(b)
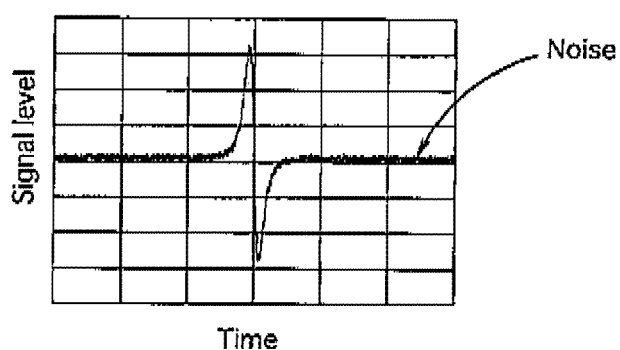

Fig. 3
(a)
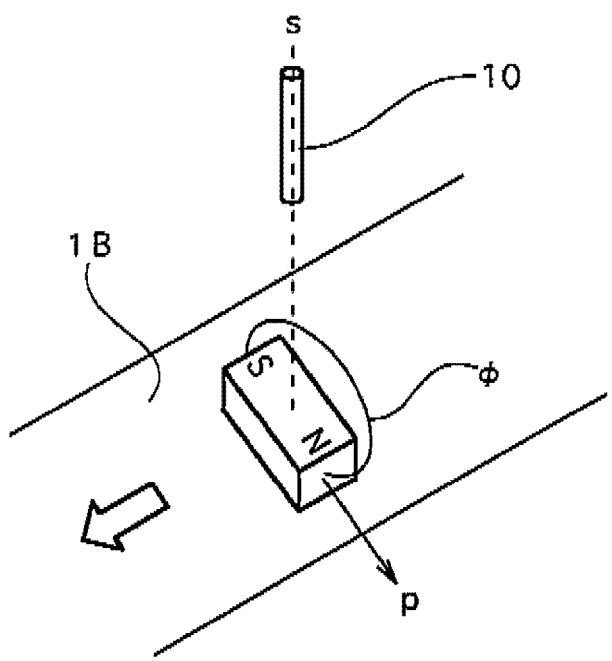
(b)
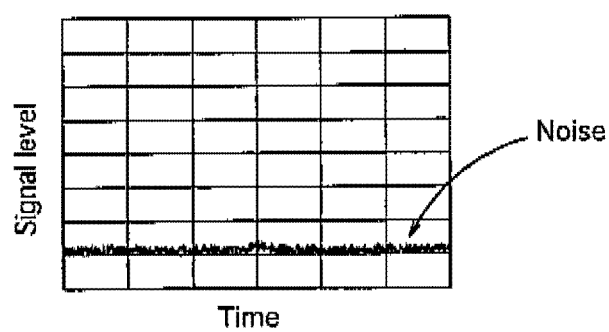

Fig. 6
(a)
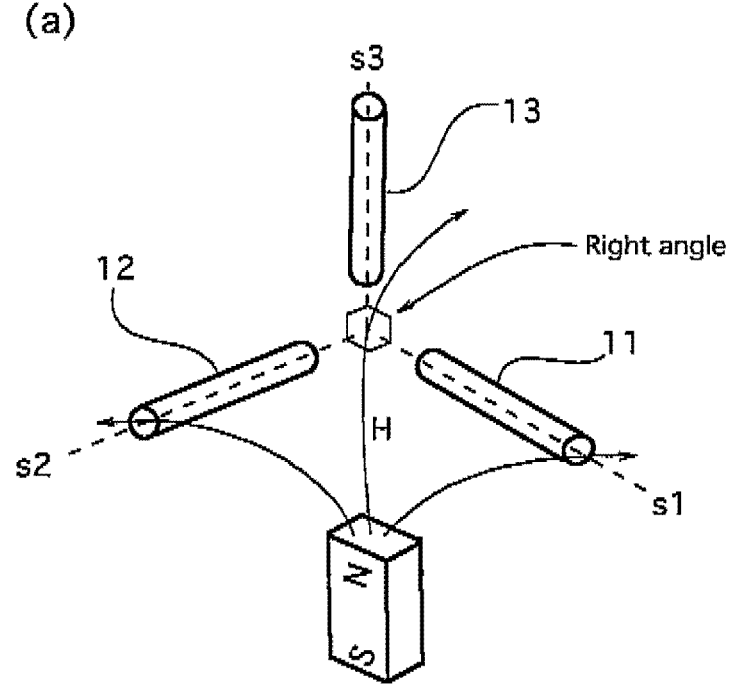
(b)
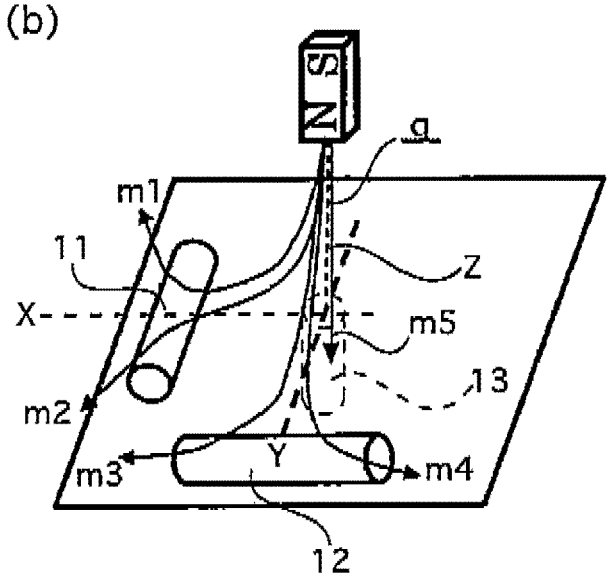

Fig. 7
(a) 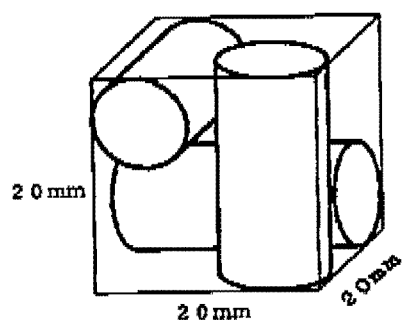
(b) 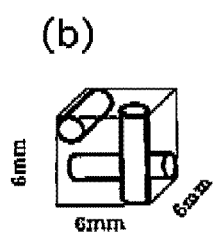
Fig. 8
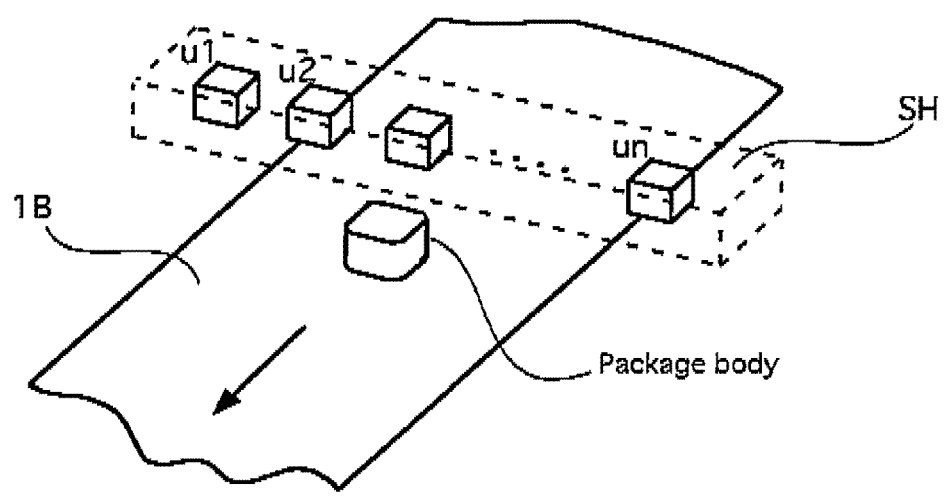

Fig. 12
(a)
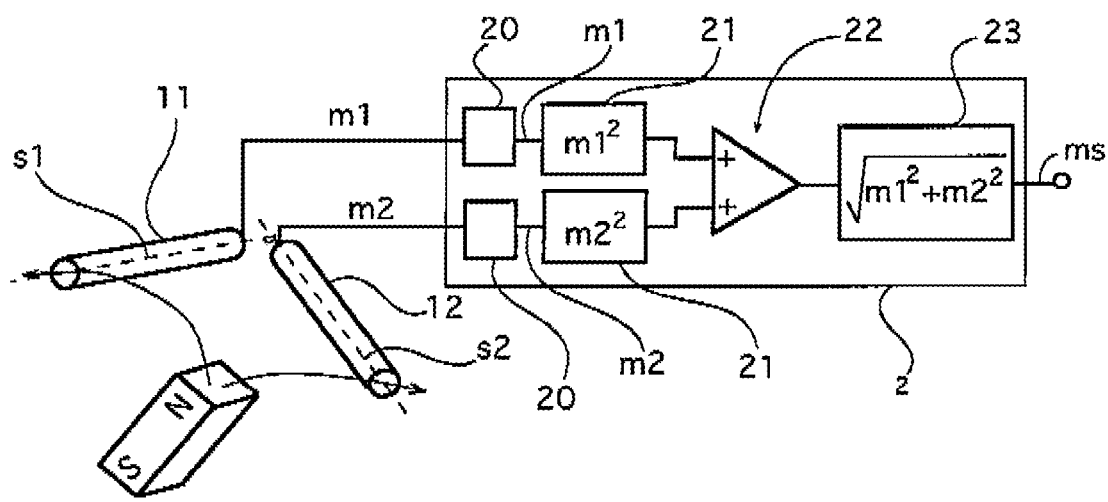
(b)
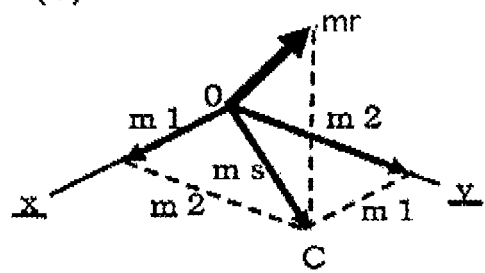

Fig. 17
(a)
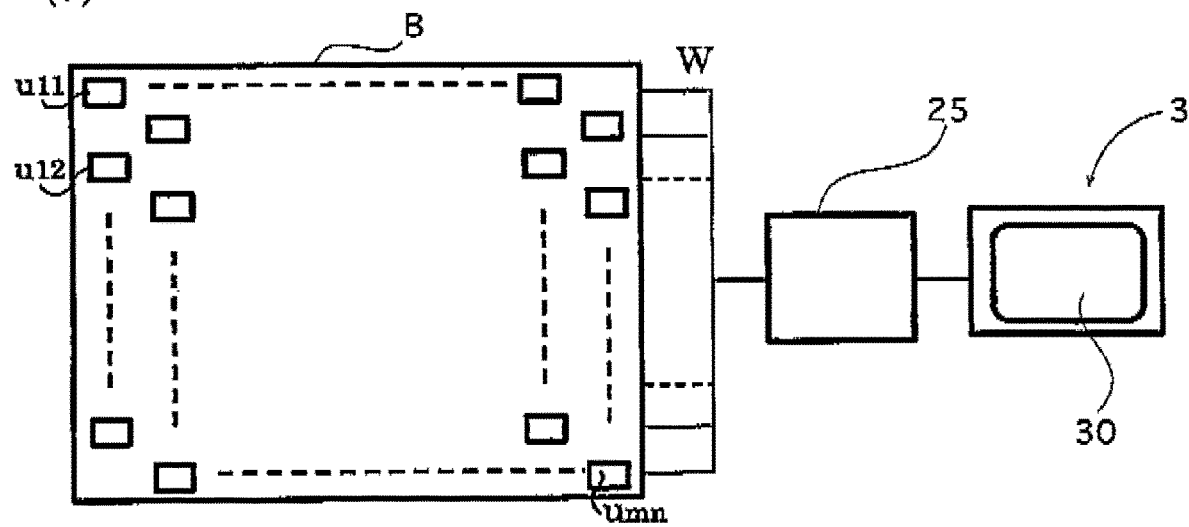
(b)
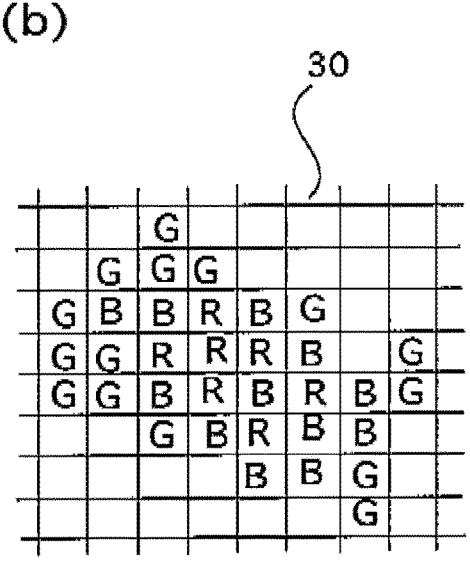
(c)
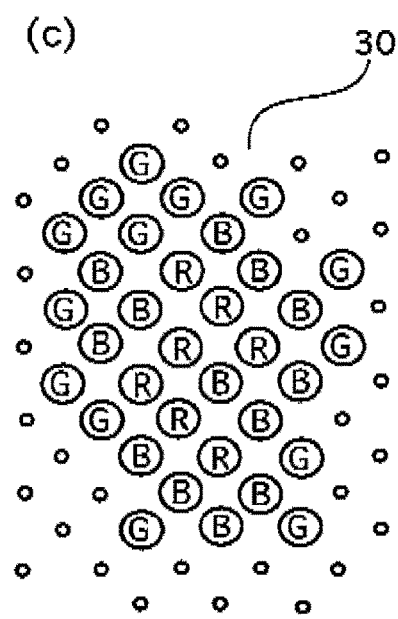

Fig. 21
(a)
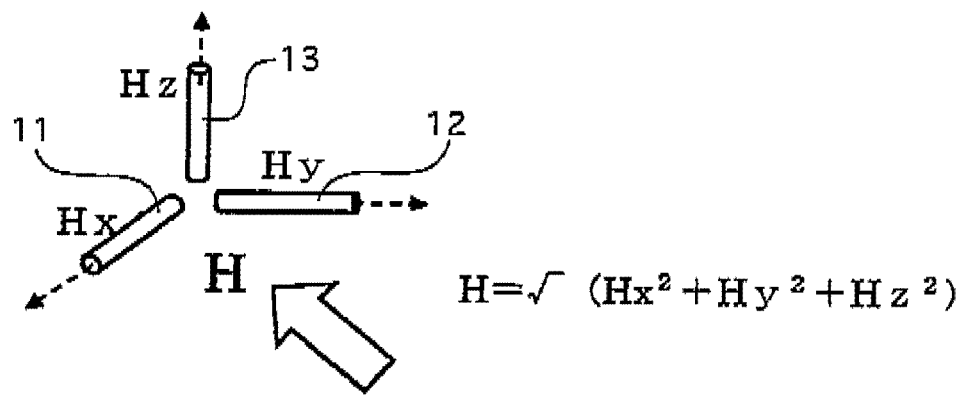
$H = \sqrt{(Hx^2 + Hy^2 + Hz^2)}$
(b)
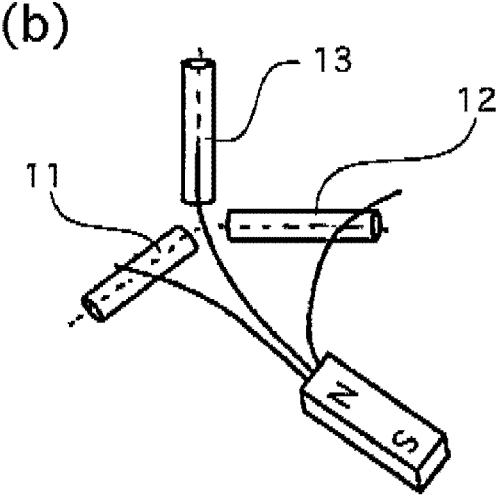

MINUTE MAGNETIC BODY DETECTING SENSOR AND FOREIGN SUBSTANCE DETECTING DEVICE

TECHNICAL FIELD OF THE INVENTION

The present invention relates to a minute magnetic body detecting sensor that detects a minute magnetic body magnetized by natural magnetization, for example, due to geomagnetism, etc., or by artificial magnetization and to a foreign substance detecting device that detects a minute magnetic body that entered as a foreign substance in an inspected object.

PRIOR ART

A conventional magnetic body detecting device includes, as shown for example in FIG. 24 (FIG. 5 of Patent Document 1), a sensor unit SU, having a plurality of fluxgate type magnetic detecting elements S distributedly disposed on a document placement surface PD on which a document can be placed, and a control box that decides whether or not a staple, etc., is attached to the document, based on detection signals from the plurality of fluxgate type magnetic detecting elements S.

As shown in FIG. 25, the fluxgate type magnetic detecting element S has an exciting coil RC and a detecting coil DC wound around a magnetic core CO, formed for example permalloy or Sendust, etc., having a soft magnetic property into an annular shape.

Also, as another conventional metal detecting device, that detects metal foreign substances in a product as an inspected object W packaged in a packaging material as shown in FIG. 26 (FIG. 10(b) of Patent Document 2) and includes a conveyor CB conveying the inspected object W within a conveying path, a magnetizing portion M magnetizing a metal m in the inspected object W, a detecting head H, having vertically opposed type sensor heads SE with a plurality of fluxgate sensors having sharp directivity in a rectangular direction rectangular to a conveying direction of the inspected object W and disposed in the rectangular direction, and detecting an rectangular direction component of residual magnetism of the metal m in the inspected object W magnetized by the magnetizing portion M, and a decision means PS that decides the existence or non-existence of the metal m in the inspected object W based on converted digital signals obtained by AD converting the detected signals from the plurality of sensor heads SE of the detecting head H detected when the inspected object W passes the detecting head H, and by referencing a threshold for decision by AD converters AS, has been proposed.

PRIOR ART DOCUMENT

Patent Literature

Patent Literature 1: JP2006189376A
Patent Literature 2: JP201429323A

SUMMARY OF THE INVENTION

Problems to be Solved by the Invention

In the conventional magnetic body detecting device described in Patent Document 1, the fluxgate type magnetic detecting element S is a so-called parallel (closed magnetic circuit type) fluxgate type element, having the exciting coil RC and the detecting coil DC wound around a vertically extending portion of the single, large, square-shaped magnetic core (core) CO, formed permalloy or Sendust, etc., having a soft magnetic property into the annular shape, and therefore the magnetic detecting element is large, a distance between adjacent sensors is thus long as shall be explained below, and there is thus a problem that there are cases where a minute magnetic body positioned between the adjacent sensors cannot be detected.

Also, when the present inventors performed numerous tests of minute magnetic body detection by a magnetic body detecting device that includes the conventional magnetic detecting element, it was found that cases arose where detection of satisfactory precision could not be performed. When the cause was investigated in detail, the findings described below were obtained.

That is, the magnetic body detecting device described in Patent Document 1 detects staples that are previously known to be positioned in a longitudinal direction at a left end of a document and although a disposition direction of the single magnetic core (core) CO, which is the magnetic body of the fluxgate type magnetic detecting element S and is formed permalloy or Sendust, etc., having a soft magnetic property into the annular shape, can thus be determined such as to detect, with satisfactory sensitivity, the staples positioned in the longitudinal direction at the left end of the document, incase the inspected object is something except staples, specifically, when a metal piece is mixed, at a state of unspecific position and orientation (angle), in a product which is the inspected object W, is to be detected, it was found that since the detection sensitivity is dependent on the relative position and orientation of the metal piece with respect to a uniaxial direction of a magneto-sensitive axis s, which is a central axis of the single magnetic core (core) C that is determined by the disposition of the core that is a magneto-sensitive body of the sensor, there arise cases where the metal piece cannot be detected if it is positioned at a position and orientation of low detection sensitivity with respect to the magnetic core (core) C of the fluxgate type magnetic detecting element.

Also, from FIGS. 2 and 3, the conventional metal detecting device of Patent Document 2 also has a single magnetic detecting element, including a single permalloy large magnetic body, disposed at a plurality of locations in a width direction of the conveying path and when such a magnetic detecting element that detects a magnetic field in a specific uniaxial direction determined by the disposition direction of a single, permalloy large magnetic body is used, a possibility of inability to detect may arise, as with the magnetic body detecting device described in the abovementioned Patent Document 1, with a magnetic body mingled at a state where relative position and orientation (angle) in an inspected object are unspecific.

Further, in the conventional metal detecting device described in Patent Document 2, if the plurality of sensors used in the sensor head SH are the parallel type fluxgate sensors shown in FIG. 25(a) as in the above-described case, the sensors are large and the distance between mutually adjacent sensors is long as shall be explained below, and there is thus a problem that a region may be present where a minute magnetic body positioned between the sensors cannot be detected.

Also, in the metal detecting device, the sensor is configured by the parallel type fluxgate sensor and the magneto-sensitive body is thus configured by a single magnetic core (core) CO of permalloy, etc., having a soft magnetic property, and there is thus a case that if a metal piece that entered in a product, which is the inspected object W, is in a state where its position and orientation are of low detection sensitivity with respect to the uniaxial direction of the magneto-sensitive axis s, which is the central axis of the single magnetic core (core) CO that is determined by the disposition of the core, it is a problem that there are cases when it may not be possible to detect the metal piece.

The present invention has been made to solve the above described problem and an object thereof is to enable reliable detection of a minute magnetic body and reliably enable detection of foreign substances of a minute magnetic body mingled at a state where positions and orientations in an inspected object are unspecific.

Means for Solving the Problems

To solve the above described problem, the present inventors focused using an amorphous wire, an amorphous ribbon, or other amorphous material that is high in detection sensitivity as a magneto-sensitive body of a magnetic detecting element and is miniaturizable and focused that there is a need to enable detection regardless of relative position and orientation of a minute magnetic body with respect to the magneto-sensitive body, and based on these noted points, came to focus on a first technical idea of the present invention to use at least two or more magneto-sensitive bodies, constituted of an amorphous material, in a single sensor such that even when a minute magnetic body cannot be detected with a single magneto-sensitive body, the minute magnetic body is detected by the other magneto-sensitive body disposed such that sensitive axes of maximum sensitivity directions of the magneto-sensitive bodies are mutually different directions. As a result of carrying out further research and development, the present inventors arrived at the present invention that reliably detects a minute magnetic body regardless of relative position and orientation of the minute magnetic body with respect to magneto-sensitive bodies in a sensor. That is, the present invention, which, even at a state where positions and orientations of foreign substances of a minute magnetic body mixed in an inspected object are unspecific, enables reliable detection of the foreign substances, was arrived at.

Also, the present inventors noted that there is a need to dispose the at least two magneto-sensitive bodies in the magnetic detecting element such as not to interfere magnetically and came to focus on a second technical idea of the present invention of disposing the magneto-sensitive bodies of the magnetic detecting element without an extended line of the sensitive axis of one magneto-sensitive body contacting (colliding) with the other magneto-sensitive bodies and arrived at the present invention that enables detection of foreign substances of a minute magnetic body without the at least two magneto-sensitive bodies interfering with each other magnetically.

Further, the present inventors arrived at an invention of a foreign substance detecting device that has a plurality of minute magnetic body detecting sensors according to the present invention disposed in a detection region and, when a minute magnetic body is positioned in the detection region, displays the minute magnetic body in a display portion of a display device corresponding to the detection region based on an output signal output by the minute magnetic body detecting sensor that detected a local magnetic field of the minute magnetic body and arrived at the present invention that enables to display existence or non-existence of foreign substances entering in an inspected object and displaying in accordance with positions and orientations of the foreign substances in the inspection region.

A minute magnetic body detecting sensor, obtained as a result of the above-described consideration, on a first aspect described in claim 1 of the present invention comprises a magnetic detecting element for outputting a voltage in response to a local magnetic field generated by a magnetized minute magnetic body positioned around a magneto-sensitive body of an amorphous material to which an electrical pulse current or an alternate current is applied, and a signal processing device for processing the voltage to output an output signal, in which the magnetic detecting element comprises at least two magneto-sensitive bodies which are disposed such that sensitive axes of maximum sensitivity directions thereof are mutually different directions.

A minute magnetic body detecting sensor on a second aspect described in claim 2 of the present invention according to the first aspect of the present invention, is configured that the at least two magneto-sensitive bodies are two-dimensionally disposed.

A minute magnetic body detecting sensor on a third aspect described in claim 3 of the present invention according to the first aspect of the present invention, is configured that the at least three magneto-sensitive bodies are three-dimensionally disposed in a space without magnetically interfering.

A minute magnetic body detecting sensor on a fourth aspect described in claim 4 of the present invention according to the second aspect of the present invention, is configured that the two magneto-sensitive bodies, which detect the local magnetic field of the minute magnetic body, are disposed without contacting in an rectangular relation along end parts of adjacent two sides on a rectangular substrate, a driver circuit, which is connected to said two magneto-sensitive bodies and applies to the electrical pulse current or the alternate current, is disposed on said substrate, and the signal processing device, which is connected to the two magneto-sensitive bodies and which processes the voltage detected by the two magneto-sensitive bodies based on the local magnetic field of the magnetized minute magnetic body, is disposed on the substrate.

A minute magnetic body detecting sensor on a fifth aspect described in claim 5 of the present invention according to the third aspect of the present invention, is configured that the three magneto-sensitive bodies which detect the local magnetic field of the minute magnetic body are disposed in three-dimensional directions such that the angle between mutual sensitive axes thereof is almost perpendicular, and the signal processing device connected to the three magneto-sensitive bodies obtains the total magnetic signal component of the local magnetic field generated by the minute magnetic body based on output signals of the three magneto-sensitive bodies.

A minute magnetic body detecting sensor on a sixth aspect described in claim 6 of the present invention according to the first aspect of the present invention, is configured that the at least two magneto-sensitive bodies are disposed without an extended line of the sensitive axis or the sensitive axis of one magneto-sensitive body contacting with the other magneto-sensitive bodies.

A minute magnetic body detecting sensor on a seventh aspect described in claim 7 of the present invention according to one of the first aspect to the sixth aspect of the present invention, is configured that a magnetic impedance element or an orthogonal fluxgate type detection element is adapted as the magnetic detecting element.

A foreign substance detecting device on an eighth aspect described in claim 8 of the present invention comprises a magnetic detecting element for outputting a voltage in response to a local magnetic field generated by a magnetized minute magnetic body positioned around a magneto-sensitive body of an amorphous material to which an electrical pulse current or an alternate current is applied, a signal processing device for processing the voltage to output an output signal, and a display device for displaying on a display portion based on an output signal of the signal processing device, in which the magnetic detecting element comprises at least two magneto-sensitive bodies which are disposed on a plane such that sensitive axes of maximum sensitivity directions thereof are mutually different directions, and a plurality of the magnetic detecting elements are disposed with distances in a detection region in the same plane, and in which the foreign substance detecting device is configured such that the signal processing device obtains the amplitude of the local magnetic field generated by the minute magnetic body by processing based on the voltage output in response to the local magnetic field of the minute magnetic body detected by the magnetic detecting element in case of a foreign substance of a magnetized minute magnetic body entering in inspected object placed on the detection region, and the display device displays the foreign substance of the magnetized minute magnetic body entering in the inspected object placed on the detection region on the display portion.

A foreign substance detecting device on a ninth aspect described in claim 9 of the present invention according to the eighth aspect of the present invention, is configured a magnetic impedance element or an orthogonal fluxgate type detection element is adapted as the magnetic detecting element.

A minute magnetic body detecting sensor of the first aspect of the present invention, having the above-described configuration, is configured that at least two amorphous material magneto-sensitive bodies, constituting the magnetic detecting element and being disposed such that sensitive axes of maximum sensitivity directions are mutually different directions, and output voltages corresponding to a local magnetic field generated by a minute magnetic body, positioned around the magneto-sensitive bodies and magnetized by magnetization by applying an electrical pulse current or an alternate current, and therefore even if the voltage output from one of the magneto-sensitive bodies is close to zero, another magneto-sensitive body, with the sensitive axis disposed in the different direction, performs detection and output voltage reliably, and thus attains an effect of enabling reliable detection of the minute magnetic body regardless of relative orientation with respect to the at least two magneto-sensitive bodies.

A minute magnetic body detecting sensor of the second aspect of the present invention, having the above-described configuration, according to the first aspect of the present invention, is configured that the at least two amorphous material magneto-sensitive bodies constituting the magnetic detecting element in the first invention have the sensitive axes, of the maximum sensitivity directions, in mutually different directions and are disposed two-dimensionally, and therefore even if the voltage output by one of the two-dimensionally disposed magneto-sensitive bodies is close to zero, another magneto-sensitive bodies, with the sensitive axes disposed two-dimensionally in the different direction, perform detection and voltage output reliably, and therefore attains an effect of enabling reliable detection of the minute magnetic body, regardless of the relative two-dimensional positions and orientations of the minute magnetic body with respect to the at least two magneto-sensitive bodies.

A minute magnetic body detecting sensor of the third aspect of the present invention, having the above-described configuration, according to the first aspect of the present invention, is configured that the at least three magneto-sensitive bodies are three-dimensionally disposed in a space without magnetically interfering, so even if the voltage output by one of the three-dimensionally disposed magneto-sensitive bodies is close to zero, any of the at least two other three-dimensionally disposed magneto-sensitive bodies performs voltage detection and output. Therefore reliable detection of the minute magnetic body is enabled regardless of the relative three-dimensional positions and orientations of the minute magnetic body with respect to the at least three magneto-sensitive bodies.

A minute magnetic body detecting sensor of the fourth aspect of the present invention, having the above-described configuration, according to the second aspect of the present invention, is configured that the two magneto-sensitive bodies, which detect the local magnetic field of the minute magnetic body, are disposed without contacting in an rectangular relation along end parts of adjacent two sides on a rectangular substrate, a driver circuit, which is connected to said two magneto-sensitive bodies and applies to the electrical pulse current or the alternate current, is disposed on said substrate, and the signal processing device, which is connected to the two magneto-sensitive bodies and which processes the voltage detected by the two magneto-sensitive bodies based on the local magnetic field of the magnetized minute magnetic body, is disposed on the substrate. Therefore detection of the minute magnetic body positioned in an inspection region is enabled by a required number of the substrates being disposed in parallel in the inspection region.

A minute magnetic body detecting sensor of the fifth aspect of the present invention, having the above-described configuration, according to the third aspect of the present invention, is configured that the three magneto-sensitive bodies which detect the local magnetic field of the minute magnetic body are disposed in three-dimensional directions such that the angle between mutual sensitive axes thereof is almost perpendicular, and the signal processing device connected to the three magneto-sensitive bodies obtains the total magnetic signal component of the magnetic field generated by the minute magnetic body based on output signals of the three magneto-sensitive bodies, therefore for any relative orientation of the minute magnetic body in three dimensions with respect to the three magneto-sensitive bodies, stable detection in accordance with the position and orientation is enabled.

A minute magnetic body detecting sensor of the sixth aspect of the present invention, having the above-described configuration, according to the first aspect of the present invention, is configured that the at least two magneto-sensitive bodies are disposed without an extended line of the sensitive axis of one magneto-sensitive body contacting with the other magneto-sensitive bodies, therefore precise detection of the minute magnetic body is enabled without the at least two magneto-sensitive bodies interfering magnetically.

A minute magnetic body detecting sensor of the seventh aspect of the present invention, having the above-described configuration, is configured that a magnetic impedance element or an orthogonal (open magnetic circuit) fluxgate type detecting element is used as the magnetic detecting element used in the first aspect to the sixth aspect of the present invention. In the minute magnetic body detecting sensor of the seventh aspect of the present invention, either type of element is a highly sensitive and miniaturizable magnetic detecting element that uses an amorphous material for the magneto-sensitive bodies and is capable of detecting the magnetic field by outputting a voltage in accordance with a strength of a magnetic field around, upon application of an electrical pulse current or high-frequency current (magnetic impedance element) or an alternate current (orthogonal fluxgate type detection element) and attains an effect of enabling precise detection of the minute magnetic body. Besides the orthogonal type, as a fluxgate sensors there is a parallel fluxgate sensor, which is frequently used conventionally and has permalloy as a core, but this type is difficult to miniaturize and therefore not suitable for the present invention.

A foreign substance detecting device of the eighth aspect of the present invention, having the above-described configuration, is configured that the magnetic detecting element, with the above-described configuration, comprises at least two magneto-sensitive bodies disposed such that the sensitive axes of the maximum sensitivity directions are mutually different directions and a plurality of the elements are disposed with a distance in the inspection region on the same plane. Therefore, when foreign substances of a magnetized minute magnetic body are positioned in the inspection region, the amplitude of a local magnetic field generated by the minute magnetic body is determined by the signal processing device performing signal processing based on the voltage output by the magnetic detecting element that detected the local magnetic field of the minute magnetic body and the display device displays, on the display portion, the minute magnetic body entering in the inspected object placed in the detection region, and thus attains an effect of enabling display in accordance with two-dimensional positions and orientations of foreign substances entering in the inspected object placed in the detection region.

Here, the amplitude of the local magnetic field generated by the minute magnetic body to be determined by the magnetic detecting element may be determined, for example in a case where there are two magneto-sensitive bodies, as a component along a plane containing the magneto-sensitive axes of the two magneto-sensitive bodies, in a case where three magneto-sensitive bodies are provided such that the magneto-sensitive axes are mutually orthogonal, it may be determined as a total magnetic force component as in the fifth invention.

A foreign substance detecting device of the ninth aspect of the present invention, having the above-described configuration, is configured that a magnetic impedance element or an orthogonal fluxgate type detection element is adapted as the magnetic detecting element as used in the eighth aspect of the present invention. And a foreign substance detecting device capable of precise detection of the minute magnetic body, by the same reason as the seventh invention described above, can be provided.

BRIEF DESCRIPTION OF THE DRAWINGS

FIG. 1a shows a perspective view and a diagram showing a relationship of relative position/orientation of a conveyed minute magnet body and a magneto-sensitive body and detected output in a first embodiment of the present invention.

FIG. 1b shows a time series signal with a large output peak.

FIG. 2a shows a perspective view and a diagram showing the relationship of the detection output in a case where the minute magnet body is disposed and conveyed with its length direction in a conveying direction in the first embodiment.

FIG. 2b shows a time series signal of a voltage waveform having positive and negative output peaks.

FIG. 3a shows a perspective view and a graph showing the relationship of the detection output in a case where the minute magnetic body is disposed and conveyed with its length direction in an orthogonal relationship with respect to the conveying direction in the first embodiment.

FIG. 3b shows a time series signal when the detection output is zero or decreases close to zero.

FIG. 6a shows a perspective view showing a disposition mode of three magneto-sensitive bodies, constituting a magnetic impedance element in a minute magnetic body detecting sensor with respect to a minute magnetic body in a third embodiment of the present invention, and a perspective view for explaining magnetic flux detection in a case where the minute magnetic body is positioned in a particular position and orientation.

FIG. 6b shows a z-axis magneto-sensitive body 13, having a sensitive axis in the perpendicular direction indicated by a broken line, provided additionally to enable detection of a z-axis component m5.

FIG. 7a shows perspective views showing disposition modes of three magneto-sensitive bodies in detecting head portions in a minute magnetic body detecting sensor in a fifth embodiment of the present invention and a conventional fluxgate sensor.

FIG. 7b shows the three magneto-sensitive bodies disposed along edge lines of a cube of 6 mm square.

FIG. 8 is a perspective view showing an application example of the minute magnetic body detecting sensor on a foreign substance detecting device that uses a belt conveyor in the fifth embodiment and a fourth example.

FIG. 12a is a block explanation diagram for explaining a signal processing device and a disposition mode of two magneto-sensitive bodies of a minute magnetic body detecting sensor of a second example of the present invention.

FIG. 12b shows a magnetic field mr generated by the minute magnet body.

FIGS. 17a, 17b, and 17c show description diagrams for explaining essential portions of the inspection platform, a microprocessor that constitutes a signal processing device, a display device, and a plurality of display modes of the display device of the fifth example.

FIGS. 21a and 21b show explanation diagrams for explaining a mode of detecting a local magnetic field of a minute magnet body when three magneto-sensitive bodies are disposed three-dimensionally in the magnetic detecting head.

DESCRIPTION OF THE EMBODIMENTS

Figure 4:
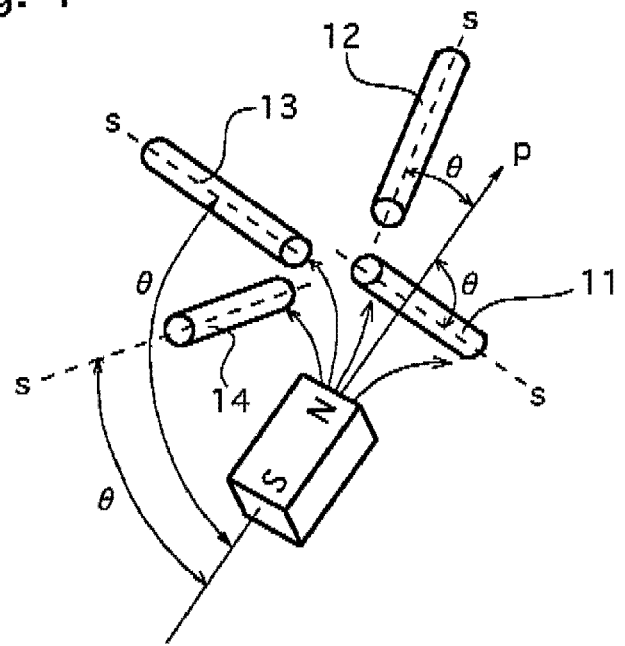
FIG. 4 is a perspective view showing a disposition mode of a plurality of magneto-sensitive bodies, constituting a magnetic impedance element in a minute magnetic body detecting sensor with respect to the minute magnetic body in the first embodiment.

Hereinafter, a best mode of the present invention will be described based on embodiments and examples with reference to the drawings.

First Embodiment

For example, an iron-based foreign substance contained in a food is a minute iron fragment, an iron ball, or an iron particle, etc. In nature, such iron substances are magnetized by geomagnetism and may thus be considered to be, so-to-speak, minute magnet bodies. Detection of such the minute magnet body is performed by using a magnetic sensor to detect a local magnetic field generated by the minute magnetic body. In recent years, demand for detecting smaller foreign substances, such as an iron ball with a diameter of 0.3 mm or even 0.1 mm, etc., is heightening.

An intensity of the local magnetic field generated becomes quickly weaker as the diameter of a magnet body decreases and in order to detect it without overlooking, a super sensitivity magnetic sensor capable of measurement of several nT (nanoteslas) or more is required to secure a sufficient signal-to-noise ratio.

Also in inspection of foreign substances in a food, a magnetic sensor must be disposed at a fixed distance away without contacting and damaging a package body or a food in an interior of a packaged product, etc., and since the intensity of the magnetic field to be detected becomes weaker with increase in distance, the magnetic sensor is required to be made even higher in sensitivity.

Under such a background, with an inspection device according to a prior art, there are cases where, depending on the state of relative positions and orientations of a minute magnet body that is a foreign substance and a magneto-sensitive body of a magnetic sensor, non-uniformity of magnitude occurs in a signal output by the magnetic sensor and the overlooking occurs.

As a result of studying the cause of the above, the following became clear.

If an iron-based foreign substance is regarded as a minute magnet body and its magnetic field, that is, its flow of magnetic flux φ is considered, it forms a local magnetic field such that the magnetic flux flows out from an N pole and curvingly returns to an S pole as shown in FIG. 1(a). That is, whereas in a vicinity of the N pole or the S pole at either end, the magnetic flux is high in density and therefore a magnetic field intensity H is high, the magnetic field intensity decreases with distance from either pole and around the magnet body, an orientation of the magnetic flux and the magnetic field intensity H variation according to location.

A magnetic axis p (axis including the N pole and the S pole) of the minute magnet body as a foreign substance generally exists with arbitrary inclinations in three-dimensional directions and therefore if a magneto-sensitive body 10 of a magnetic sensor is fixed in a predetermined orientation, it detects the magnetic field H of the minute magnet body as a directional component along a sensitive axis (axis along which sensitivity is maximum) s of the magneto-sensitive body.

Therefore, if a relative angle formed by the magnetic axis p of the minute magnet body and the sensitive axis s of the magneto-sensitive body 10 is θ, a magnetic input into the magneto-sensitive body 10 when the external magnetic field around the magneto-sensitive body is H is Hx cos θ. Here, if as mentioned above, the directions of the magnetic axis and the sensitive axis are substantially matched, that is, if the relative angle θ is substantially 0, cos θ is substantially 1, and the product of the external magnetic field H and cos θ is thus substantially H such that a magnetic field substantially equivalent to the intensity H of the peripheral magnetic field is input into the magneto-sensitive body of the magnetic sensor and an output signal also corresponds to H.

Oppositely, if the relative angle θ increases and becomes close to 90°, cos θ is substantially 0 and the product with the peripheral magnetic field H is thus also substantially 0 such that the input of the magnetic field into the magneto-sensitive body 10 decreases and the signal output is small or 0.

That is, even if the distance between the minute magnet body and the magneto-sensitive body 10 is the same, the detection signal, that is, the detection output variation in magnitude in a range of 0 to H depending on the relative angle θ formed by the magnetic axis p of the minute magnet body and the sensitivity direction s of the magneto-sensitive body.

As an example of a case where a large detection signal is acquired, an example where a package body and a minute magnet body inside it are conveyed by a belt conveyor 1B in the direction of the arrow in FIG. 1(a) mentioned above shall be described.

In a case where the magnetic sensor, with the sensitive axis s of the magneto-sensitive body 10 set perpendicularly, detects the magnetic field of the minute magnet body, when the minute magnet body passes substantially directly below the magneto-sensitive body with the magnetic axis p of the magnet body being approximately perpendicular, the flow in the magnetic axis direction among the magnetic flux of the magnet body and the sensitivity direction of the magneto-sensitive body of the magnetic sensor are substantially matched such that the relative angle is substantially 0, cos θ is thus substantially 1 as indicated above, and the product with the peripheral magnetic field H is thus H, and therefore the detection signal is hardly attenuated and a time series signal is of a waveform with a large output peak as shown in FIG. 1(b).

Also, when the minute magnet body passes directly below the magneto-sensitive body 10 with the magnetic axis p of the minute magnet body being oriented in the running direction of the belt conveyor 1B as shown in FIG. 2(a), the perpendicular component of the strong magnetic field (magnetic flux) emitted from the two poles of N and S of the magnet body is detected by the magneto-sensitive body of the magnetic sensor such that a large signal output is obtained. In this case the time series signal is of a voltage waveform having positive and negative output peaks as shown in FIG. 2(b) because the two poles of N and S at the respective ends of the magnet body differ in sign.

An opposite example where a small signal is acquired is a case where, as shown in FIG. 3(a), a central portion of the minute magnet body passes directly below the magneto-sensitive body of the magnetic sensor, that is, directly below the sensitive axis with the magnetic axis p of the minute magnet body being parallel to the belt conveyor 1B and in a right angle direction with respect to the running direction of the belt conveyor. That is, the flow of the magnetic flux φ of the magnet body and the sensitive axis s of the magneto-sensitive body of the magnetic sensor are at a right angle, that is, the relative angle is substantially 90° such that cos θ is thus substantially 0 as indicated above and the product with the peripheral magnetic field H is thus also substantially 0, and therefore the magnetic input into the magneto-sensitive body is zero or extremely small, the detection signal output is zero or decreases close to zero, and the time series signal is as shown in FIG. 3(b). In such case, a foreign substance, that is, a minute magnet body is not detected even if it is present, a so-called dead angle occurs, and overlooking occurs in the inspection.

Such a problem is due to attempting to perform foreign substance inspection by using a magnetic sensor, with a sensitive axis direction of a single magneto-sensitive body being fixed, to detect a minute magnet body in a predetermined region and is an unavoidable problem.

The waveforms shown in FIGS. 1 to 3 described above not simply illustrate waveforms predicted from the description above but illustrate results confirmed by experiments upon actually preparing the above-described environments artificially. In particular, the waveform shown in FIG. 3(b) illustrates a limit of measurement with the conventional foreign substance detecting device using a magnetic sensor capable of measurement along just a single axis and illustrates important data leading to the completion of the present invention.

With a first embodiment of the present invention, based on the above-described study, a plurality of magneto-sensitive bodies of a magnetic sensor are used for a region, on which a conventional magnetic sensor performed detection using a single magneto-sensitive body, and are disposed such that their respective sensitive axis directions, which are the maximum sensitivity directions, are mutually different directions to detect a magnetic field of a minute magnet body oriented in an arbitrary direction as the plurality of different sensitive axis direction components to enable detecting without bringing dead angle depending on circumstances of relative positions and orientations of the minute magnet body and the magneto-sensitive bodies of the magnetic sensor, and by using magnetic signals detected by the respective magneto-sensitive bodies or by mutually signal processing the respective signals, omission-free, highly precise detection of the minute magnet body is enabled.

Further with the first embodiment, due to the magnetic sensor using the plurality of magneto-sensitive bodies, a signal level obtained by performing signal processing is high and minute magnet body detection of high sensitivity is enabled.

Although with the first embodiment, an example of performing detection of foreign substances in a package body was described, applications to detection of an object that generates a local magnetic field, for example, detection of staples and magnetic ink in a document, detection of iron powder in a film, detection of iron components in a powder, measurement of magnetic pattern, etc., may be considered as applications of the first embodiment.

The first embodiment may also be used for measurement of biomagnetic phenomena, such as magnetoencephalography, magnetocardiography, etc.

The minute magnetic body detecting sensor of the first embodiment uses a magnetic impedance element having a plurality of amorphous material magneto-sensitive bodies as shown in FIG. 4 and since a single region is measured by disposing the respective sensitive axes s to be oriented in mutually different directions, even if a minute magnet body is contained in an inspected object in a state where its magnetic axis p is oriented in an arbitrary direction, the respective magneto-sensitive bodies 11 to 14 of the magnetic sensor detect its magnetic field as components in the directions of the respective sensitive axes s and respectively output output signals.

Therefore, on the minute magnetic body detecting sensor of the first embodiment, even when one of the magneto-sensitive bodies cannot output an output signal of significant magnitude, another magneto-sensitive body is able to output an output signal of significant magnitude and when output signals of significant magnitude are output by all of the magneto-sensitive bodies, the minute magnet body can be detected with high precision and high sensitivity by performing signal processing using all of the output signals, thus exhibiting an effect of enabling realization of an overlooking-free foreign substance detecting device.

Second Embodiment

Figure 5:
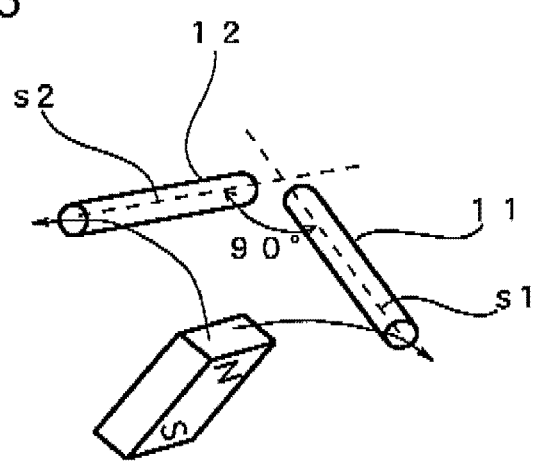
FIG. 5 is a perspective view showing a disposition mode of two magneto-sensitive bodies, constituting a magnetic impedance element in a minute magnetic body detecting sensor with respect to a minute magnetic body in a second embodiment of the present invention.

As shown in FIG. 5, a minute magnetic body detecting sensor of a second embodiment uses a magnetic impedance element having two amorphous material magneto-sensitive bodies 11 and that are disposed such that the angle formed by the respective sensitive axes s1 and s2 is substantially 90° (in substantially two dimensions) and therefore the local magnetic field generated by the minute magnet body oriented in an arbitrary direction is detected by the two magneto-sensitive bodies 11 and 12 as components in the directions of the respective sensitive axes s1 and s2.

On the minute magnetic body detecting sensor of the second embodiment, since the magnetic flux of the local magnetic field of the minute magnet body is curved, sensitive axis direction components appear respectively in the two magneto-sensitive bodies in accordance with the movement of the minute magnet body, contained in the package body, by a belt conveyor, etc., and therefore by detecting these components and by signal processing from either of the signals of the two magneto-sensitive bodies 11 and 12 or using the two signals from the two magneto-sensitive bodies 11 and 12 together, dead-angle-free, highly precise detection of the minute magnet body is enabled by the magnetic impedance element having only two magneto-sensitive bodies 11 and 12 and an effect of enabling the realization of an overlooking-free foreign substance detecting device is exhibited.

Third Embodiment

As shown in FIG. 6, with a minute magnetic body detecting sensor of a third embodiment, three magneto-sensitive bodies 11, 12 and 13 of a magnetic sensor are disposed such that angles formed by the respective sensitive axis directions are substantially 90° (in substantially three dimensions) and a local magnetic field generated by a minute magnet body oriented in an arbitrary direction is thereby detected by the three magneto-sensitive bodies 11, 12, and 13 as components in the respective sensitive axis directions and the detection signals are output.

When a minute magnet body (with NS being oriented in a perpendicular direction) is positioned on a perpendicular line q that intersects an intersection of broken lines passing through length direction midpoints of the magneto-sensitive bodies 11 and 12 in the rectangular relationship in the second embodiment described above, magnetic fluxes m1 and m2, m3 and m4 that pass through the two magneto-sensitive bodies 11 and 12 as shown in FIG. 6(b) are respectively of the same magnitudes (same in distance passed and angle) and directed in directions of both ends of the magneto-sensitive bodies. The two ends of a magneto-sensitive body are mutually opposite in polarity and therefore the outputs of the magneto-sensitive bodies 11 and 12 are zero and the magnet body thus cannot be detected in this state.

However, with the third embodiment, a z-axis magneto-sensitive body 13, having a sensitive axis in the perpendicular direction indicated by a broken line, is provided additionally to enable detection of a z-axis component m5 as shown in FIG. 6(b). That is, as shown in FIG. 21, a magnetic field H oriented in an arbitrary direction can be detected by synthesis of three directional components Hx, Hy, and Hz in three-dimensional directions x, y, and z and the magnetic field (total magnetic force) H at the location at which the sensor is placed can thus be determined by performing square-root calculation of the sum of square values $Hx^2$, $Hy^2$, and $Hz^2$ of the three directional components Hx, Hy, and Hz. That is, regardless of the direction in which the local magnetic field H due to the minute magnet body is oriented in any direction, dead-angle-free magnetic measurement is enabled with the sensor head having the three magneto-sensitive bodies 11, 12, and 13 disposed three-dimensionally.

Sum of the three detected signal components corresponds to the total magnetic force component of the local magnetic field H at the location at which the magneto-sensitive bodies are placed, and all of the directional components of the local magnetic field H in the three dimensional space that is the location, at which the three magneto-sensitive bodies 11, 12, and 13 are placed, are thus detected without omission, without dependence on circumstances of relative positions and orientations of the minute magnet body and the magneto-sensitive bodies 11, 12, and 13 of the magnetic sensor, a foreign substance detecting device, that is highly stable, more highly sensitive, and omission-free by signal processing from the detection signal of any of the magneto-sensitive bodies or using the three detection signals from the magneto-sensitive bodies 11, 12, and 13 together, and attains an effect of enabling realization.

Fourth Embodiment

On the minute magnetic body detecting sensor of any of the first to third embodiments, an operation, such as synthesis, filtering, averaging, enhancement, etc., may be performed as the signal processing using the respective detection signals of the plurality of magneto-sensitive bodies in the magnetic sensor together (fourth embodiment) and a more highly precise magnetic signal can thereby be obtained, and thus attains an effect of enabling omission-free detection of a minute magnet body that is not influenced by magnetic background noise.

Fifth Embodiment

A minute magnetic body detecting sensor of a fifth embodiment is a magnetic sensor, in which a magnetic core comprising an amorphous wire or an amorphous ribbon is used as a magneto-sensitive body of a magnetic impedance element of the magnetic sensor in any of the first to fourth embodiments. The amorphous wire has, for example, a diameter of several 100 μm or less and a length of several 10 mm or less and typically a length of several mm, the amorphous ribbon has a thickness of several 100 μm or less, a width of several mm or less, and a length of several 10 mm or less and typically a length of several mm, and both, although having such extremely small dimensions, have high magneto-electric conversion abilities and therefore enable construction of an ultra-compact magnetic sensor head.

For example, to consider an example of housing the magneto-sensitive bodies of a magnetic sensor in a space of the smallest volume while disposing them in substantially three dimensions (three directions) as in a case where a plurality of head portions, with the magneto-sensitive bodies serving a central role, are disposed in parallel, a disposition, where as shown in FIGS. 7(*a*) and (*b*), outer dimensions (occupied space dimensions) of a three-dimensional magnetic sensor head, in which the three magneto-sensitive bodies are combined such that angles formed mutually by the magneto-sensitive axes that are the central axes thereof are 90 degrees, are those of a cube with one side being of a length of each magneto-sensitive body, may be considered as a disposition that minimizes a size of an entirety of the head portion in a state where the magnetic axes of the three magneto-sensitive bodies do not mutually interfere mechanically and magnetically.

Figure 25:
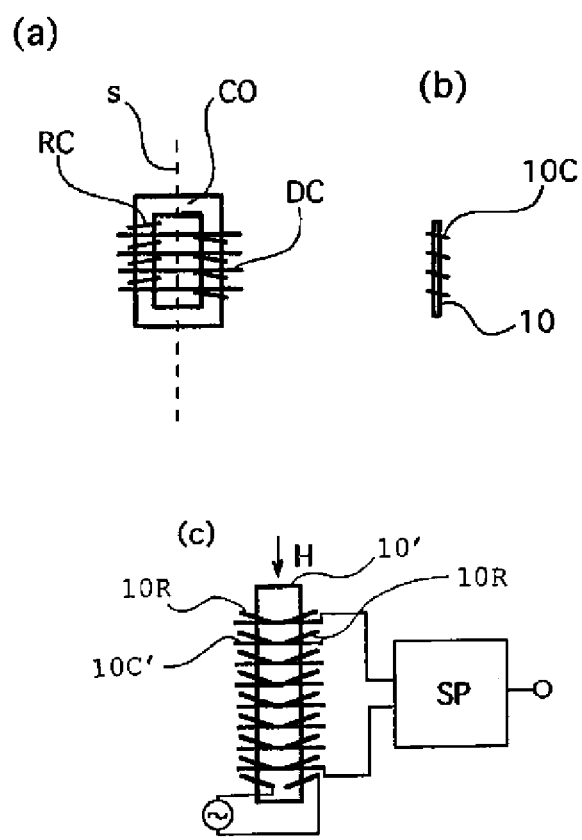
FIGS. 25a, 25b, and 25c show explanation diagrams for explaining basic structures of a parallel fluxgate type magnetic detecting element in the conventional staple detection device, an MI magnetic sensor of the fifth embodiment, an orthogonal fluxgate type magnetic detecting element of a sixth example, and a parallel fluxgate type magnetic detecting element of a modification example.
Figure 26:
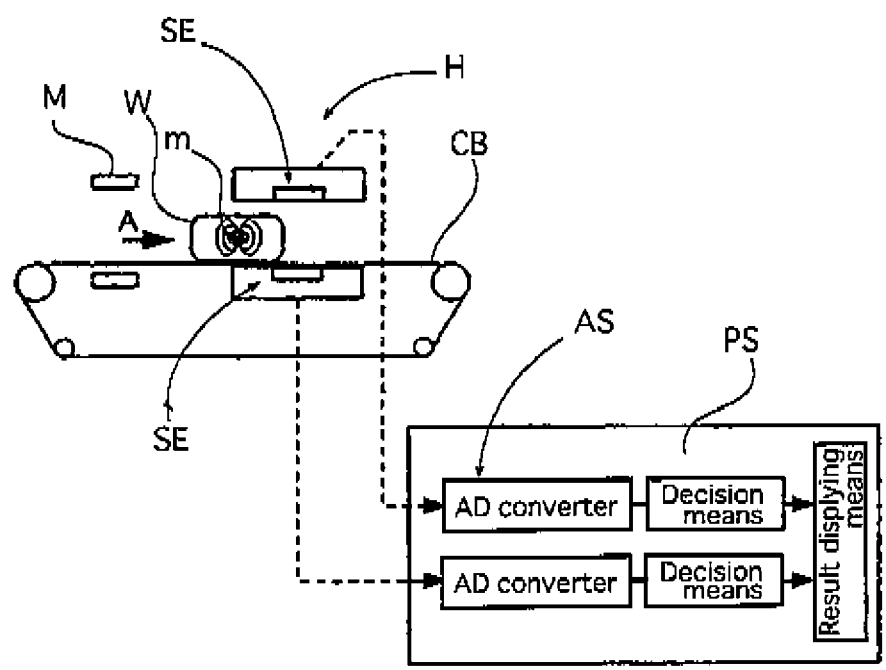
FIG. 26 is a description diagram for explaining a conventional metal detecting device using parallel fluxgate type magnetic detecting elements.

On a head (MI element) of an MI magnetic sensor (magnetic impedance sensor), capable of measurement of a several nT level and having an amorphous material, such as an amorphous wire, as a magneto-sensitive body, for example in an MI magnetic sensor as shown in FIG. 25(*b*), a head portion has a simple structure where an amorphous wire with a diameter of approximately 10 μm and a length of approximately 6 mm is fixed to abase and has a coil wound thereon and therefore the magnetic sensor head portion can be made to have a length of approximately 6 mm and an average diameter of 1.5 mm.

On the other hand, a head portion of a fluxgate magnetic sensor, which is capable of measurement of a level of several nT, is high in sensitivity, and is said to be most compact, is large size, with a length of 20 mm and a diameter of 10 mm. Typically with a magneto-sensitive body of such a conventional, so-called parallel fluxgate sensor, a closed magnetic circuit structure is constructed in the same manner as a transformer with a high permeability material, such as permalloy, and since a complex structure where two or three coils of an exciting coil RC and a detecting coil DC are wound around a single, large core CO, disposed in a certain direction, is configured, it becomes large, and it was confirmed that if a three-dimensional magnetic sensor head is configured by disposing the magneto-sensitive bodies of this parallel fluxgate sensor in three-dimensional directions, it would be as shown in FIG. 25(*a*) and difficult to configure compactly as in the MI magnetic sensor with a single coil 10C wound around the amorphous wire core as shown in FIG. 25(*b*) or an open magnetic circuit type orthogonal fluxgate sensor.

The combination head portion of the MI magnetic sensor in the fifth embodiment is 6 mm×6 mm×6 mm at the minimum because the magneto-sensitive bodies are disposed along edge lines of a cube of 6 mm square as shown in FIG. 7(*b*), a three-dimensional head configured with the conventional type fluxgate sensors is 20 mm×20 mm×20 mm, and width dimensions of the three-dimensional heads of the respective sensor types are 6 mm on the MI magnetic sensor of the fifth embodiment and 20 mm on the conventional type fluxgate magnetic sensor head.

Here, to illustrate an example of practical application to a foreign substance detecting device, if a minute magnet body existence internally in a package body conveyed by a belt conveyor is to be detected, a plurality of sets of magnetic sensor units (three-dimensionally disposed heads) u1 to un must be disposed in a direction crossing the belt conveyor 1B, which is the conveying path, in a sensor holding device SH as shown in FIG. 8 in consideration of an intensity of magnetism generated by the minute magnet body, a height (distance) from the belt at which the magnetic sensor is disposed, an area i.e. view radius on the belt surface across which the magnetic sensor can perform magnetic detection effectively.

Here, it is required that a detection sensitivity of the minute magnet body must be of a fixed level or more and be substantially uniform within the magnetic field detection view area of each sensor unit without occurring of an inspection overlooking regardless of which position within the width of the belt conveyor 1B the minute magnet body to be detected is existed, that is, regardless of the position which the minute magnet body passes with respect to the plurality of magnetic sensors (the magneto-sensitive bodies that are the magnetic heads) that are disposed.

Figure 9:
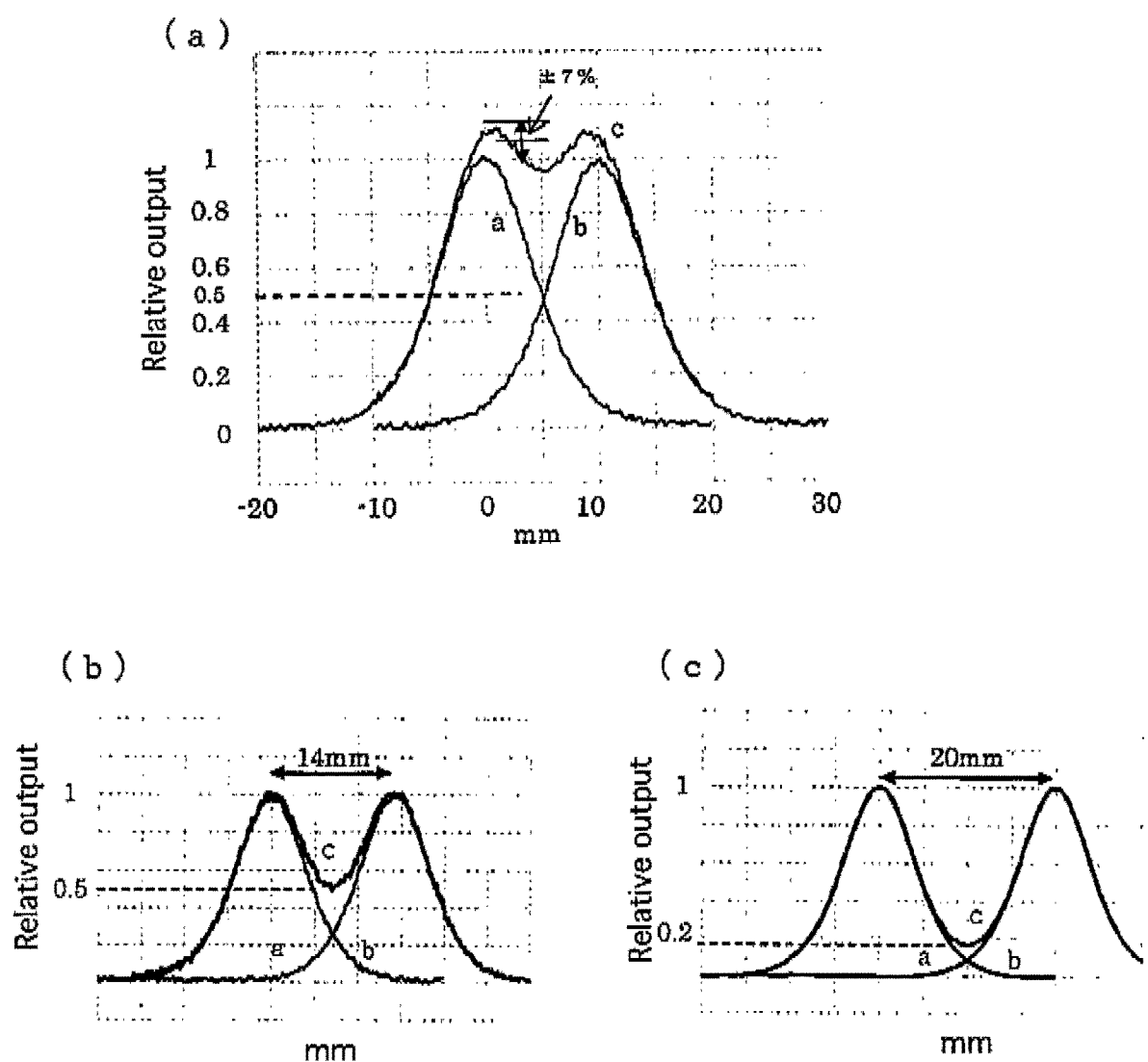
FIGS. 9a, 9b, and 9c show graphs showing distribution diagrams of summed outputs of detection outputs of detection by two magneto-sensitive bodies, disposed in two, mutually-adjacent three-dimensional magnetic detecting heads when the distance between the two magneto-sensitive bodies is changed to 10 mm, 14 mm, and 20 mm.

In FIG. 9(*a*), an output of a magnetic impedance element when a minute magnet body is moved right and left (− to +of the abscissa in FIG. 9) with respect to a position directly below a magneto-sensitive body (0 position of the abscissa) as a center is shown as an example indicated by the symbol a, and it is shown, with the output corresponding to approximately 30 nT (nanoteslas) when the minute magnet body is directly below the magneto-sensitive body being 1, that the output decreases when the minute magnet body is moved to the right and left. This example is that of detecting a 0.2 mm iron ball, and when the minute magnet body, that is, the iron ball is moved 5 mm to the right or left, the output decreases by approximately 50% and the output attenuates towards zero as the iron ball is moved in a direction further away from the 0 position.

When, in this state, the same measurement is performed with a magneto-sensitive body of another magnetic impedance element being disposed adjacently away by 10 mm and its output is displayed, it has the shape of a waveform substantially similar to that of the symbol a but shifted 10 mm to the right as indicated by the symbol b in FIG. 9(*a*).

Here, when the signals of the two mutually adjacent magnetic sensors are summed, the result is a waveform having two peaks as indicated by the symbol c in FIG. 9(*a*), with a maximum value being 1.03, a minimum value being 0.95, and a variation with respect to an average value falling within approximately ±7%, and thus even if the iron ball moves by 5 mm, the signal does not vary considerably, and therefore regardless of at what position within the magnetic field detection range of the sensor unit the minute magnet body is present, it can be detected with substantially the same sensitivity.

Therefore, omission-free foreign substance detection can thus be realized by disposing magnetic sensors at every 10 mm across the entire width direction of the belt conveyor 1B as described above.

Such disposition of the magneto-sensitive bodies, that is, the magnetic detecting heads at every 10 mm is enabled, as mentioned above, by a magnetic sensor, that is, an MI magnetic sensor with an amorphous wire or an amorphous ribbon, as an amorphous material, as a magneto-sensitive body or by an open type orthogonal fluxgate magnetic sensor (vertical type fluxgate magnetic sensor), differing in magnetic circuit from the conventional art and being rod-shaped, with the magnetic flux flowing out into air as shown in FIG. 25(*b*) is realized. Also, the MI magnetic sensor having the amorphous wire as the magneto-sensitive body or the open magnetic circuit type orthogonal fluxgate sensor has another feature of being extremely inexpensive in the manufacturing cost due to having a simple structure where a wire is simply wound around a coil and thus provides the merit of not causing significant cost increase with respect to the entire foreign substance detecting device even if used in large numbers.

On the other hand, as described above, the conventional closed magnetic circuit type parallel fluxgate magnetic sensor, with which the magnetic flux does not flow out into air due to the magnetic circuit being closed due to the magnetic circuit having a square shape as one form of an annular shape as shown in FIG. 25(b), is large in size and therefore does not enable the detection head to be disposed at every 10 mm and therefore does not enable the realization of a foreign substance detecting device such as that of the fifth embodiment and is also expensive such that a cost increase cannot be avoided if used in large numbers.

The above description illustrates an example where non-uniformity of signal magnitude (sensitivity) due to sum computation of the signals of two magnetic sensor units can be minimized by overlapping the magnetic field detection ranges of both at portions where the sensitivities of the respective sensor units are substantially 50%.

However, in foreign substance detection, whether a magnetic field intensity of a certain magnitude or more is "present" or "not present" is determined and therefore usually, whether or not a magnetic signal magnitude (level) is clearly dissociated from a threshold is determined and a difference of sensitivity of several % or several dozen % is not considered to present a major problem in many cases in consideration that a difference of such level is masked by noise.

For example, when as in an example shown in FIG. 9(b), the distance between the magneto-sensitive bodies of the mutually adjacent sensor units of symbols a and b is spread to approximately 14 mm and the sensitivities are mutually overlapped at approximately 25%, the minimum sensitivity of symbol c in FIG. 9(b), which indicates the sum of the detection signals of the magneto-sensitive bodies of the two sensor units of a and b, becomes approximately 50% of the maximum value. It is thus considered that such method of use is also possible if the sensitivity variation does not have to be set very strictly.

In a case of using the conventional type parallel fluxgate sensor, the distance between sensors spreads to 20 mm or more as mentioned above and by a similar estimation, as shown in FIG. 9(c), the minimum output (sensitivity) of the symbol c, which indicates the sum of the detection signals of the magneto-sensitive bodies of the two mutually adjacent sensor units of the symbols a and b in FIG. 9(c), becomes 20% or less of the maximum value and cannot be said to be very practical.

That is, as is clear from FIG. 9(c), a region where the sensitivity is 50% or less extends for 10 mm and there is thus a possibility of occurrence of detection omission of a minute magnetic body positioned in that region.

Thus, with the application example of the present embodiment, a plurality of sensor heads can be constructed with extremely small dimensions using a magnetic core including an amorphous wire or an amorphous ribbon as a magneto-sensitive body, making it possible to dispose a sensor head, including magneto-sensitive bodies enabling magnetic field detection in two directions or more plural directions, in a fixed region (for detection of a diameter of, for example, several mm to several dozen mm), conventionally detected with a single sensor, to detect the minute magnet body without overlooking.

Also, an MI magnetic sensor that uses an amorphous wire has ultrahigh sensitivity and is therefore capable of detecting a magnetic field of a minute magnet body with an intensity of several hundred pT or a lower magnetic field such that by using a magnetic shield cylinder of permalloy material, etc., to shield the magnetic sensor and a package body from magnetic noise of the surroundings, detection of extremely small iron foreign substances or foreign substance detection from a remote position is further enabled.

Although in the above description, an example of combining magnetic heads, which are magneto-sensitive bodies, in three dimensions in a space of the smallest volume was described, if, in a case of disposing a plurality of sensor units, that is, magneto-sensitive bodies, a distance slightly wider than 10 mm is allowed, three sensors, each assembled integrally on an electronic circuit substrate, may be combined as they are to configure a three-dimensional magnetic sensor unit.

Figure 10:
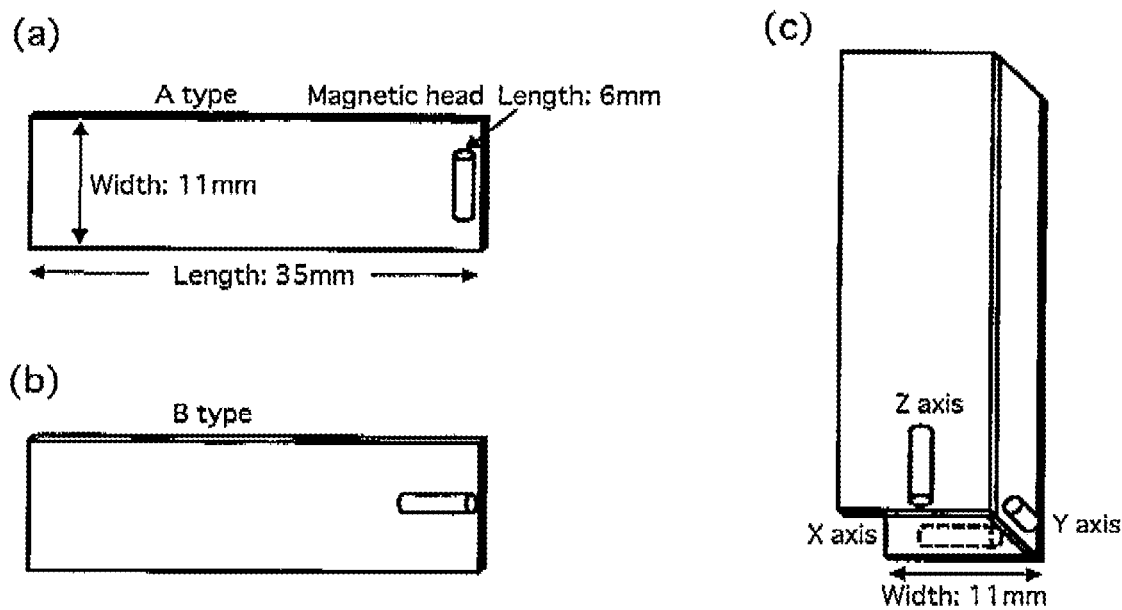
FIGS. 10a, 10b, and 10c show plan views and a perspective view showing the other examples of rectangular substrates constituting another three-dimensional magnetic detecting head.

As the abovementioned sensor, there are present the two types of an A type, in which a magnetic head is installed in parallel to a width direction at one end in a length direction of an electronic circuit board, and a B type, in which a magnetic head is installed in parallel to a length direction atone end in the length direction of an electronic circuit substrate, as shown in FIGS. 10(a) and (b). In FIGS. 10(a) and (b), just the electronic circuit substrate and the MI magnetic sensor head are illustrated representatively.

A three-dimensional magnetic sensor that measures the three axial directions X, Y, and Z can also be realized by combining the substrates of the abovementioned two types of sensors by disposing two of the A type and one of the B type in a U shape as shown in FIG. 10(c).

With the present magnetic sensor, since the electronic circuit substrates of both the A type and B type have a width dimension of 11 mm and a length dimension of 35 mm, a minimum width dimension as a three-dimensional magnetic sensor unit is 11 mm.

First Example

Figure 11:
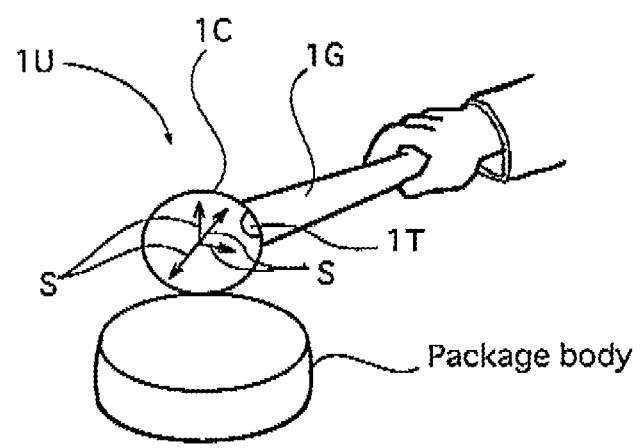
FIG. 11 is a perspective view showing an outer appearance and an inspection state of a minute magnetic body detecting sensor of a first example of the present invention.

As shown in FIG. 11, a minute magnetic body detecting sensor of a first example includes a sensor unit 1U, including a plurality of magneto-sensitive bodies with respective sensitive axes s thereof disposed indifferent directions, and a grip rod 1G, with the sensor unit disposed at a tip end and a grip portion formed at another end, and is configured such that a user grips the grip portion to bring the sensor unit at the tip end close to an inspected object and moves it along a surface to detect a minute magnetic body of a mingled foreign substance. The sensor unit 1U is housed in a sensor cover 1C.

The sensor unit 1U is configured such that a plurality of magneto-sensitive bodies 11 to 14 are disposed in random directions on one plane or three magneto-sensitive bodies are disposed in three-dimensional directions as shown in FIG. 4 or FIG. 6, detection signals are signal processed by an unillustrated signal processing device placed in the sensor cover 1C, and when a detection signal of a fixed level or more is output, a lighting portion 1T, disposed at a portion of the sensor cover IC is lit.

To detect a foreign substance, that is, a minute magnet body contained in a package body of the inspected object, the sensor cover is brought close to the package body and moved along a surface of the package body, and when foreign substances of the minute magnet body are thereby detected, the lighting portion 1T is lit.

On the minute magnetic body detecting sensor of the first example, the sensitive axes s of the plurality of the magneto-sensitive bodies or magnetic sensors are disposed in mutually difference directions, thus exhibiting an effect of enabling oversight-free inspection regardless of in which direction a minute magnet body is oriented in the package body or regardless of how the grip rod is held (orientation, inclination).

Second Example

As shown in FIG. 12, with a minute magnetic body detecting sensor of a second example, two magneto-sensitive bodies, constituting a magnetic impedance element, are disposed in substantially two-dimensional directions (two-dimensional plane) whereby an angle formed by the respective sensitive axes s1 and s2 is substantially 90 degrees, and a local magnetic field, due to a minute magnet body that is a foreign substance, is calculated, in a signal processing device 2, as a magnetic component ms in a plane containing the two sensitive axes by using output signals m1 and m2 of a signal processing circuit 20, which processes and amplifies damped oscillating voltages output from the two magneto-sensitive bodies (magnetic sensors), and by squaring each signal by two square computing elements 21, then adding by an adder 22, and then computing the square root by a square root computing element 23.

On the magneto-sensitive bodies 11 and 12, the sensitive axes s1 and s2 are disposed in two dimensions in one plane with the respective maximum sensitive axes being the x and y axes such that a mutually formed angle is 90 degrees. A magnetic field mr generated by a minute magnet body that is a detection object is shown in FIG. 12(b), an intensity of its component in the x-y plane is ms, and it is detected as the two components of a component m1 along the sensitive axis s1 detected by one magneto-sensitive body 11 and a component m2 along the sensitive axis s2 detected by the magneto-sensitive body 12.

That is, when the magnitudes of m1 and m2 detected by the two magneto-sensitive bodies 11 and 12 are expressed by the lengths of the arrows in FIG. 12(b), the lengths from the tips of the respective arrows to an intersection C of two broken lines drawn at right angles with respect to the respective axes are respectively equal to m2 and m1. Therefore, the length ms of an arrow joining the intersection C and the 0 point is the magnetic component determined by square root computation of the arrow ms, from 0 with C as its tip, the square root being determined upon adding the square value of m1 and the square value of m2 according to the theorem of a right-angled triangle, and when a perpendicular line is dropped from the tip of the local magnetic field mr, generated by the abovementioned magnet body, it contacts the point C in the abovementioned two-dimensional plane.

On the minute magnetic body detecting sensor of the second example, since a magnetic field of a minute magnet body is a local magnetic field and a magnetic component ms, passing through the plane containing the two sensitive axes s1 and s2, is thus always present in a return path of the magnetic flux, by calculation of this component, it is a component of a magnetic field mr of the minute magnet body along the plane containing the magneto-sensitive axes s1 and s2 of the two magneto-sensitive bodies (for example, a horizontal plane in FIG. 10(b)), and therefore an effect of enabling realization of an overlooking-free, highly precise device for inspection of presence or non-presence of a minute magnet body is attained.

Third Example

Figure 13:
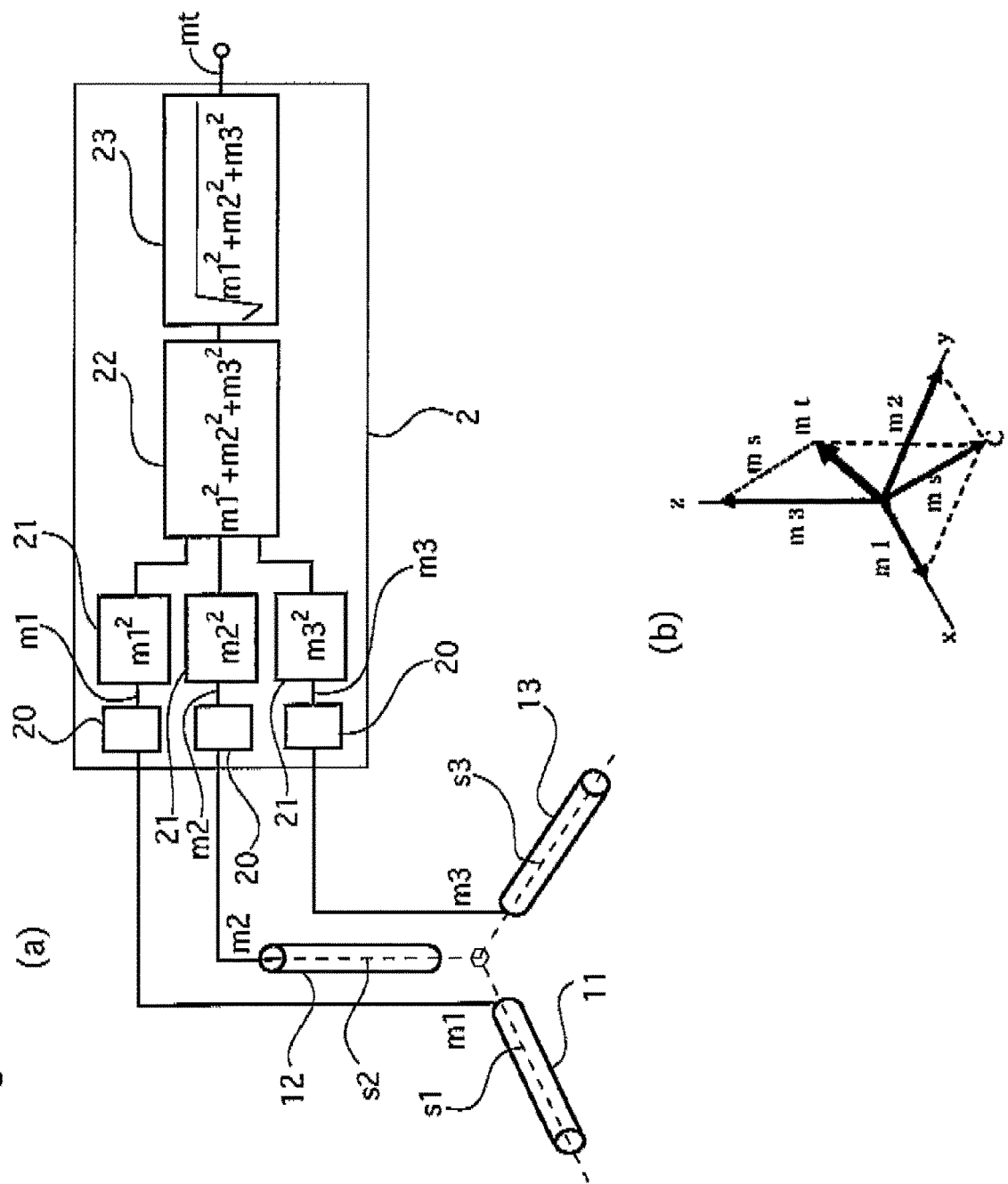
FIG. 13a is a block explanation diagram for explaining a signal processing device and a disposition mode of three magneto-sensitive bodies of a minute magnetic body detecting sensor of a third example of the present invention.
FIG. 13b shows that a sum of square values of output signals m1, m2, and m3, which are components along magneto-sensitive axes of the three magneto-sensitive bodies 11 to 13 that are disposed in three dimensions, is calculated and the total magnetic signal component mt is calculated as the square root, corresponds to the magnetic field generated by a magnet body.

As shown in FIG. 13(a), with a minute magnetic body detecting sensor of a third example, angles formed by respective sensitive axes s1, s2, and s3 of three magneto-sensitive bodies 11 to 13, constituting a magnetic impedance element, are set in substantially three-dimensional directions to be substantially 90 degrees, and, as in the second example described above, a magnetic field generated by a foreign substance that is a minute magnet body is calculated as a total magnetic signal component mt corresponding to the magnetic field generated by the minute magnet body by using output signals m1, m2, and m3 of a signal processing circuit 20 that are based on damped oscillating voltages output from the three magneto-sensitive bodies 11 to 13 and squaring each signal by a square operating element 21 to determine $m1^2$, $m2^2$, and $m3^2$, obtaining a sum of the square values by an adder 22, and calculating a square root of the sum of the square values by a square root operating element 23 by signal processing of a signal processing device 2.

As shown in FIG. 13(b), the sum of the square values of the output signals m1, m2, and m3, which are components along the magneto-sensitive axes of the three magneto-sensitive bodies 11 to 13 that are disposed in three dimensions, is calculated and the total magnetic signal component mt is calculated as the square root, corresponds to the magnetic field generated by the magnet body.

The total magnetic signal component mt is the magnetic field intensity that is decided by the distance between the magnet body and the magneto-sensitive bodies 11 to 13, that is, the relative position of the magnet body with respect to the magneto-sensitive bodies 11 to 13 and since an increasing or decreasing change of signal according to the angle formed by a sensitive axis of a magneto-sensitive body or a magnetic sensor and the minute magnet body is thus no longer present, an effect of enabling realization of a foreign substance detecting device of high stability and high precision is attained.

A mode is also possible where the presence or non-presence of foreign substances is determined from the information of $(m1^2+m2^2+m3^2)$ without performing the square root calculation performed in the signal processing device 2. A mode is also possible where the presence or non-presence of foreign substances is decided from the magnitudes of the individual signals of m1, m2, and m3 without even performing a squaring calculation, and a mode is also possible where the presence or non-presence of foreign substances is determined by performing multiplication of cubed and fourth power values as enhancement processes.

Fourth Example

Figure 14:
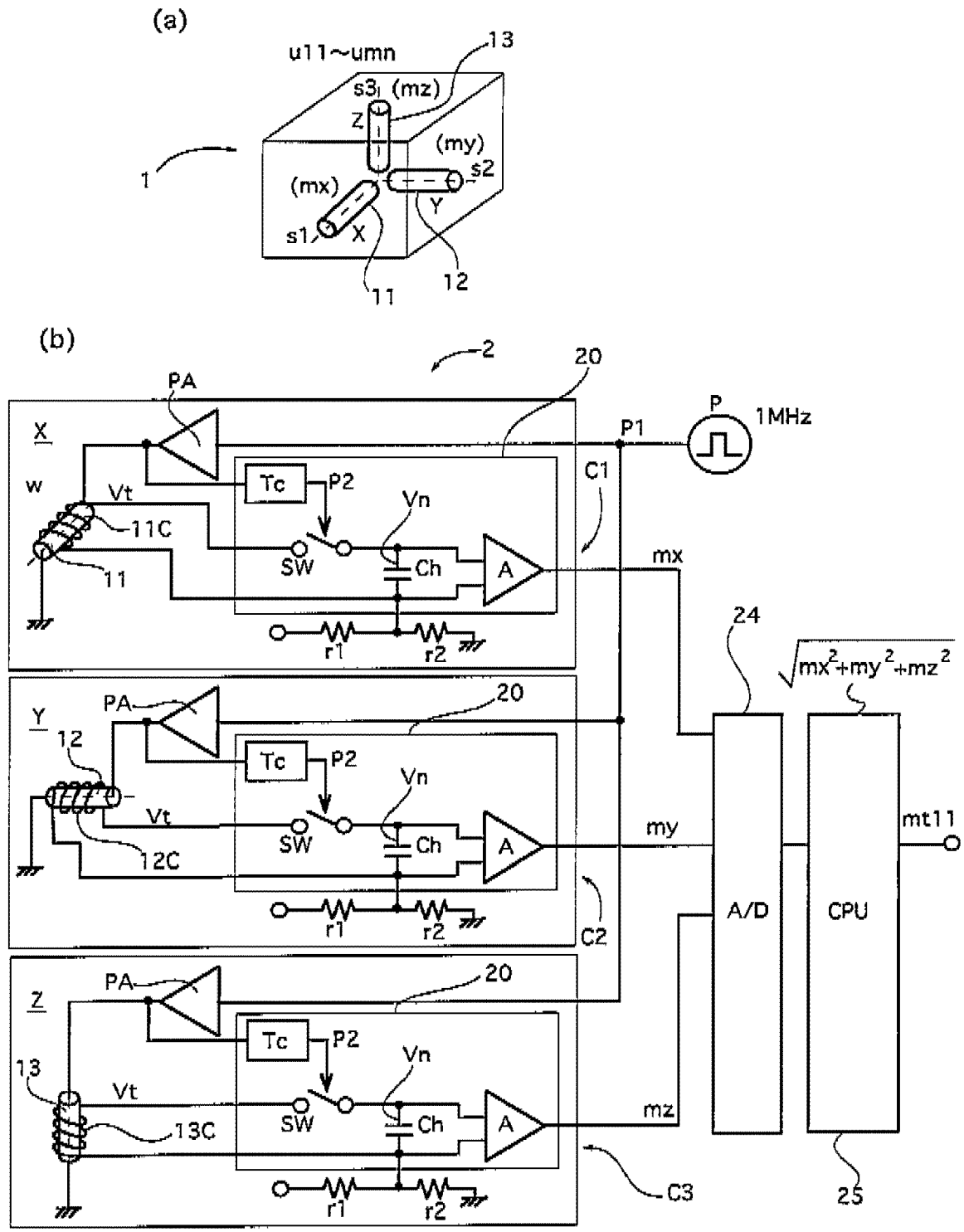
FIGS. 14a and 14b show a perspective view and a detailed circuit diagram showing a three-dimensional magnetic detecting head and a signal processing device of a foreign substance detecting device of a fourth example of the present invention.

As shown in FIG. 8 and FIG. 14, with a foreign substance detecting device of a fourth example, a plurality of sensor units u11 to umn of a magnetic impedance element 1 configured by disposing respective sensitive axes of three MI magnetic sensors in substantially three-dimensional directions such as to be substantially rectangular are used and the plurality of sensor units are disposed above a belt conveyor 1B, conveying a package body, at a height without interfering with the package body and across a width of the belt conveyor 1B to detect the presence or non-presence of foreign substances of a minute magnet body contained in the package body that passes through.

The sensor units u11 to umn are disposed across the belt conveyor 1B in the width direction at distances such that respective sensor unit detection regions overlap partially without forming a blank in a region measured by the respective units. Although aligned in a single lateral line with respect to a movement direction of the belt conveyor 1B in FIG. 8, the sensor units u11 to umn do not have to be so and may be shifted and disposed in a front/rear direction of the belt conveyor 1B. Also, the sensor units u11 to umn may be disposed at a lower portion of the belt conveyor 1B or may be disposed at an upper portion and a lower portion of the belt conveyor 1B at the same time.

As shown in FIG. 14(a), with each of the sensor units u11 to umn, the sensitive axes s1, s2, and s3 of the three magneto-sensitive bodies 11 to 13 of a MI magnetic sensor are disposed substantially along the three-dimensional directions of x, y, and z directions.

The magneto-sensitive bodies 11 (X), 12 (Y), and 13 (Z), which are the detecting elements disposed in the x, y, and z directions that are the magneto-sensitive bodies of the MI magnetic sensor that are disposed in the three-dimensional directions as shown in FIG. 14(a), are configured for being driven and performing of signal processing by an electrical circuit shown in FIG. 14(b).

In a signal processing device in the fourth example, driving circuits PA that drive the respective magneto-sensitive bodies 11, 12, and 13 disposed in three dimensions are connected to an external pulse oscillation circuit P that outputs pulses P1 of 1 MHz as shown in FIG. 14(b) and are configured to input the pulses P1 supplied from the pulse oscillation circuit P and output drive pulses of 1 MHz amplified to pulses of a predetermined voltage to the connected magneto-sensitive bodies 11, 12, and 13.

As shown in FIG. 14(b), timing circuits Tc are connected to output terminals of the driving circuits PA and control terminals of analog switches SW, to be described below, and are configured to output control pulses P2, synchronized with the pulses P1 output by the pulse oscillation circuit P, to the control terminals of the analog switches SW.

Three signal processing circuits 20 that constitute the signal processing device 2 include the analog switches SW, having input terminals connected to the magneto-sensitive bodies 11, 12, and 13 disposed in the x direction, y direction, or z direction and configured to output damped oscillating voltages, output by detecting coils 11C to 13C, wound around the magneto-sensitive bodies 11, 12, and 13, in response to a local magnetic field generated by a minute magnetic body positioned around the magneto-sensitive bodies 11, 12, and 13, from output terminals in synchronization with the inputs of the control pulses P2 output from the timing circuit Tc, hold capacitors Ch, having one end connected to the output terminals of the analog switches SW, having another end connected to a junction point of resistors r1 and r2 that divide a power supply voltage to supply a bias voltage, and holding the damped oscillating voltages output from the analog switches SW upon being output by the detecting coils 11C to 13C wound around the magneto-sensitive bodies 11, 12, and 13, and amplifiers A, connected to the output terminals of the analog switches SW, amplifying the damped oscillating voltages of the x direction, y direction, and z direction output from the analog switches SW upon being output by the detecting coils 11C to 13C wound around the magneto-sensitive bodies 11, 12, and 13, and outputting magnetic signals mx, my, and mz of three directional components.

An A/D converter 24 has input terminals connected to the output terminals of the respective amplifiers A of the signal processing circuits 20 and is configured to convert the input magnetic signals mx, my, and mz of three directional components to digital signals and output the digital signals to a microprocessor 25.

The microprocessor 25 is configured to perform squaring calculation of the digitized magnetic signals mx, my, and mz to determine $mx^2$, $my^2$, and $mz^2$, respectively, obtaining of the sum $mx^2+my^2+mz^2$, and then calculating the square root $\sqrt{(mx^2+my^2+mz^2)}$ in accordance with a program.

The operation shall be described below. The MI magnetic sensors, which are the magnetic impedance elements 1 placed in the sensor units u11 to umn, are all the same and therefore the three magneto-sensitive bodies in the sensor unit u1 shall be described representatively here.

Respective amorphous wires w, which are the magneto-sensitive bodies 11, 12, and 13, disposed in the x, y, and z directions of an MI element, are applied with pulses by the pulse amplifier PA that receives the pulses P1 supplied from the external pulse oscillation circuit P. Across both ends of the coils 11C, 12C, and 13C wound around the respective amorphous wires w, damped oscillating voltages Vt, with amplitudes in response to an external magnetic field around the amorphous wires, are generated due to an MI (magneto-impedance) effect at an instant at which a pulse current flows.

By the analog switches SW connected to one end of the coils 11C, 12C, and 13C, the damped oscillating voltages are made to be held at a predetermined timing by the holding capacitors Ch. The voltages Vh of the hold capacitors Ch are the magnetic signals corresponding to the sensitive axis direction components of the external magnetic field around the magneto-sensitive bodies 11, 12, and 13 disposed in the x, y, and z directions.

The magnetic signals are renewed each time the pulse is repeated and the respective amorphous wires w, constituting the MI elements of the respective sensor units from u1 to un and disposed in the x, y, and z directions, are all applied with pulses simultaneously in correspondence to the pulses P1 supplied from the pulse oscillation circuit P. All magnetic sensors thereby perform magnetic detection simultaneously and can be mutually prevented from being affected by noise from other sensors.

Here, a rate of repetition of the pulses P1, that is, a frequency of the pulse oscillation circuit is 1 MHz. The timing at which the analog switches SW open and close and the hold capacitors Ch hold the damped oscillating voltages is determined by the pulses P2 of the timing circuit Tc that are synchronized with the pulses P1 of the pulse oscillation circuit P.

The bias voltages generated by dividing the voltage of the power supply voltages due to the resistors r1 and r2 are supplied to the analog switches SW through the coils 11C, 12C, and 13C.

The magnetic signals, in response to the directional components of the external magnetic field around the amorphous wires w disposed in the x, y, and z directions of the MI element, are respectively subject to predetermined amplification by the amplifiers A and the magnetic signals mx, my, and mz of the three directional components are thereby output. The packages C1, C2, and C3, in which above-described magnetic impedance element 1, constituting the MI magnetic sensor, and the signal processing circuits 20 are disposed, have the same configurations.

The respective magnetic signals mx, my, and mz, detected by the magneto-sensitive bodies 11, 12, and 13 are converted to digital signals by the A/D converter, thereafter input into the microprocessor 25, the microprocessor 25 performs signal processing to compute $\sqrt{(mx^2+my^2+mz^2)}$, and consequently outputting as the total magnetic force component mt11 of the external magnetic field measured by the sensor unit u11. Similarly, mt12 to mtmn are output from the respective units.

Based on the above, a decision is made by a decision device due to the microprocessor 25 in accordance with software, and if as a result, the minute magnet body is detected, a lamp of display is lit and a warning is made by buzzer sound in accordance with an output from the microprocessor 25.

With the foreign substance detecting device of the fourth example that attains the above operations, the above-described signal processing at the signal processing circuits 20 constituted of electrical circuits and the microprocessor 25 that constitute the signal processing device 2 is applied to each of the sensor units u11 to umn, and ultimately, the total magnetic signal components mt11 to mtmn of the respective sensor units are obtained, judgment by a software-based judgment device is made based thereon, and if as a result, the minute magnet body is detected, a display lamp is lit and a warning is made by buzzer sound as an output from the microprocessor 25, and therefore an effect of realizing a foreign substance detecting device, which is overlooking-free by detection of a local magnetic field of a minute magnet body and has a simple configuration without a magnetizing means, is attained.

Fifth Example

Figure 15:
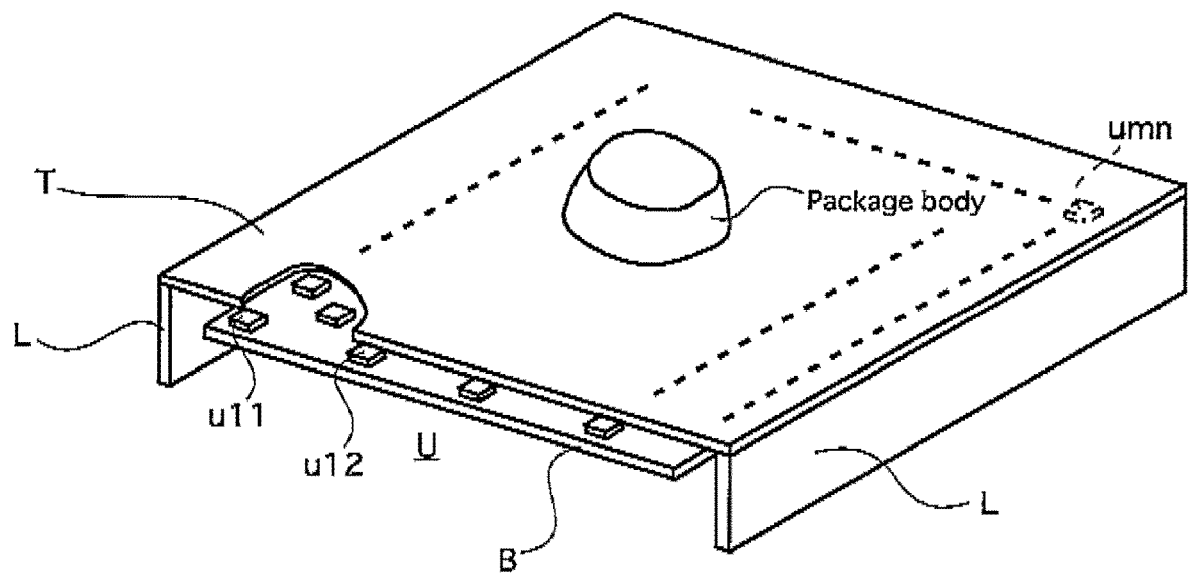
FIG. 15 is a perspective view showing an inspection platform of a minute magnetic body detecting sensor of a fifth example of the present invention.
Figure 16:
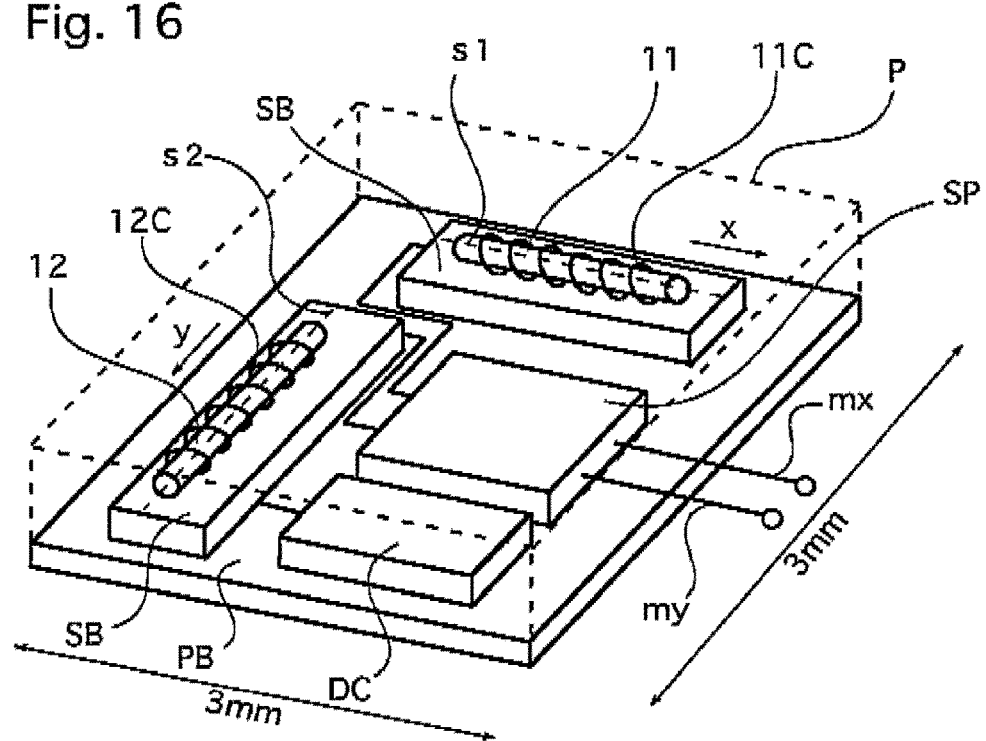
FIG. 16 is a perspective view showing a package of a sensor unit arranged in a row in a substrate of the inspection platform of the fifth example.

As shown in FIG. 15 and FIG. 16, with a foreign substance detecting device of a fifth example, a plurality of two-dimensional magnetic sensors, configured by disposing two magneto-sensitive bodies of an MI magnetic sensor as a sensor unit in substantially two-dimensional directions such that the respective sensitive axes are substantially rectangular, are used and these are disposed two-dimensionally on a lower surface of a table to detect the presence or non-presence of a foreign substance including a minute magnet body contained in a package body or a packaged product placed on an upper surface of the table.

As shown in FIG. 15, a table T, having both ends supported by two opposing leg portions L, is for placing a package body, and on a substrate B disposed at a position of fixed distance therebelow are placed the sensor units U (u11 to umn), and in one example, 18 units are arrayed in a longitudinal direction and 32 units are arrayed in a lateral direction. In regard to a vertical direction positional relationship of the table T and the substrate B, a mode where at least one of either is fixed by a height adjustment screw, etc., or where vertical positions are made adjustable by means of a driving motor (not shown) to enable adjustment in accordance with a display state on a screen or where, in order to minimize the distance, the substrate B that is a separate member from the table T is eliminated and the plurality of sensor units U are laid underground in the upper surface of the table T may be adopted.

The two-dimensional magnetic sensor unit U has a compact, two-dimensional MI magnetic sensor, manufactured by MEMS (Micro Electro Mechanical Systems) IC technology, placed and disposed in a single package P and constitutes a magnetic sensor of high sensitivity despite being of a size, for example, of approximately 3 mm×3 mm×1 mm.

As shown in FIG. 16, in the interior of the package P of the sensor unit, magneto-sensitive bodies 11 and 12, having detecting coils 11C and 12C wound therearound, are disposed on substrates SB disposed in the two-dimensional directions x and y on a package substrate PB, and a driving circuit DC, for driving in common the magneto-sensitive bodies 11 and 12 of the two MI elements, and a signal processing circuit SP, performing signal processing and conversion to digital outputs, are disposed on the package substrate PB, and signal outputs mx and my of the x and y directions that are output successively from the package P are magnetic signals, with which detection outputs of the detecting coils 11C and 12C, corresponding to an amplitude of a local magnetic field of a minute magnetic body that is an external magnetic field around the magneto-sensitive bodies 11 and 12 of the MI elements have been digitized.

The signals of the two-dimensional magnetic sensor that include the total of 576 arrayed sensor units U are taken out to the exterior by a printed wiring of the substrate B and signal processed by an external microcomputer 25 as shown in FIG. 17.

Specifically, with each sensor unit U, the square root of the sum of squares, that is, $\sqrt{(mx^2+my^2)}$ is calculated based on the magnetic signals mx and my of the magneto-sensitive detectors 11 and 12 of the x and y directions and is obtained a horizontal component of a local magnetic field due to a minute magnet body of foreign substances.

In a display screen 30 of a display device 3, the magnitudes of the horizontal components are displayed by a total of 576 display points corresponding to the two-dimensionally arrayed sensor units U by a two-dimensional variable density display, a color-coded display, a contrast display, or a numerical display of gradation, etc.

Display method of signal processing and an inspection result on the foreign substance detecting device, configured by two-dimensionally arraying the packages P that are the units u11 to umn that are the sensors having the magneto-sensitive bodies 11 and 12 disposed in the two-dimensional directions of x and y, shall now be described.

In FIG. 17, magnetic information data of the sensor units u11 to umn are successively taken into the microcomputer 25 via a cable W from the substrate B, on which the plurality of sensor units are placed, and by a data processing function of a computer software, the magnitudes of the respective magnetic signals detected are classified, one point at a time, into levels, for example, of five stages or eight stages in an order starting, for example, from weak magnetic intensity, and segments, corresponding to the array of the sensor units, are arrayed on the display screen 30 of the display device 3 to perform color-coded display in color or contrast display or variable density display.

Figure 18:
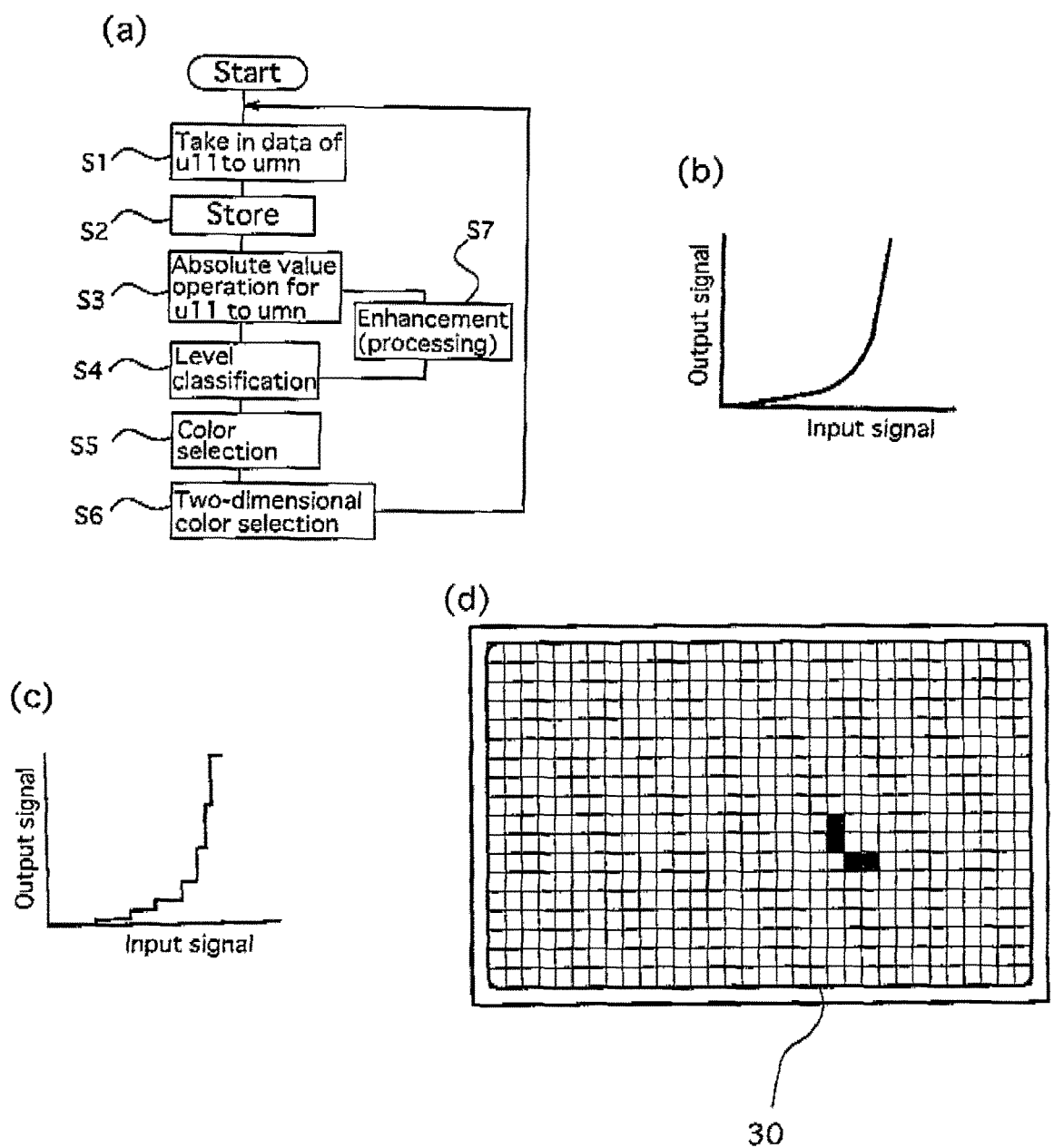
FIGS. 18a, 18b, 18c, and 18d show chart diagrams for explaining process for absolute value operation, level classification, and color selection for color-coded display in the microprocessor that constitutes the signal processing device in the fifth example.

The signal processing shall be described in accordance with the flowchart shown in FIG. 18. The magnetic data (magnetic intensities) detected by the sensor units u11 to umn are taken in successively in step S1 and stored in step S2.

In step S3, the stored data are read and an absolute value processing is performed. Here, as the absolute value operation, there is a mode where, based on the x and y magnetic signal outputs mx and my detected by the two magneto-sensitive bodies constituting the magnetic sensor incorporated in each of the sensor units u11 to umn, $mx^2$ and $my^2$ are determined by squaring to remove the plus/minus signs and then output in order to calculate the square root of the sum of squares of the respective outputs, that is, $\sqrt{(mx^2+my^2)}$ to determine the magnetic component in the plane containing the two magneto-sensitive bodies x and y and make the respective outputs be |mx| and |my| by removing the plus/minus signs, and a mode where output is performed after applying, as step S7, a signal enhancing processing that enhances a small signal to be smaller and a large signal to be larger.

This absolute operation converts all signals to be of the same polarity because, depending on the orientation of the minute magnet body, a signal polarity of a signal detected by a magnetic sensor may be positive or negative in correspondence to N and S. This is based on a technical recognition that, regardless of positive polarity or negative polarity, if an absolute value is large, it corresponds to the foreign substance being large.

In step S4, the absolute-value-converted data or the enhancement-processing-applied data are subject to successive classification of the signal magnitudes into magnetic field intensity levels of five stages or eight stages, and in step S5, colors, for example, white, yellow, green, blue, and red, corresponding to the respective levels of the five stages or eight stages are allocated to the corresponding segments, that is, display points to perform color-coded display. In FIG. 17(b), which is an enlarged view of a color-coded display portion, the character "R" for Red is displayed for red of a fifth stage, "B" for Blue is displayed for blue of a fourth stage, and "G" for Green is displayed for green of a third stage in the segments, that is, the display points.

In step S6, color display is performed according to each of the segments of the array corresponding to the sensor units in the color display screen 30 and a return to step S1 is set to perform renewal to subsequent new data.

Although the method of level classification of five stages uses, for example, the five stages of 0 to <50 nT, 50 nt to <100 nT, 100 nT to <500 nT, 500 nT to <1000 nT, and 1000 or more, depending on the inspected object, the classification levels may need to be adjusted and therefore a function for changing the levels as suitable is provided. Therefore, division into finer levels can be performed easily to change the number of stages from the level classification of five stages to the level classification of eight stages.

A method, where the magnetic field intensity levels for level classification are determined and stored in advance according to each stage number and can be changed by designating a stage number, or a method, where the magnetic field intensity levels for level classification can be set and adjusted upon viewing a display state of a minute magnetic body, etc., may be considered.

If the magnetic field generated by a foreign substance is strong or if the sensitivities of the magnetic sensors are high, even if the size of the foreign substance is small, the color-coded display (luminance display) displayed on the display is displayed larger, that is, at a large number of display points across an area wider than the actual size of the foreign substance due to the local magnetic field and magnetic flux generated around the foreign substance being detected by a plurality of sensors therearound, and although this is not a problem if it suffices to detect the presence or non-presence of foreign substances, in a case where positions of mixed foreign substances are to be grasped precisely, the positions of the foreign substances may be unclear because the color-coded display is displayed at the display points that are the 34 segments corresponding to the 34 sensors in FIG. 17(b).

To avoid this, the strongest signal or group thereof can be enhanced to display approximate two-dimensional positions of foreign substances by applying, as necessary, an enhancement operation processing described below to the detected magnetic signals in step S7 as shown in FIG. 18.

Although by squaring the detected magnetic signals as in the above-described absolute value processing, signals of low level can be made smaller and signals of high level can be made larger as shown in FIG. 18(b), operation of cubed values and fourth power values may also be performed as necessary. Signals of high level may also be made larger by applying a nonlinear operation processing to the detected magnetic signals. Further, the steps of level classification of the detected magnetic signals may be made unequal in interval such that a step is made lower for a low level and a step is made higher for a high level.

Also, if there are a plurality of display points of maximum luminance (maximum signal level) in the display screen 30, an approximate position of a foreign substance may also be narrowed down by obtaining a luminance center of gravity and displaying the position at the corresponding display points in the display screen 30. FIG. 18(d) shows an example of results of determining the luminance center of gravity as an enhancement processing and shows that a position of a foreign substance is clarified by being narrowed down and displayed at a total of four display points consisting of two points of red of the fifth stage indicated by "R" and two points of blue of the fourth stage indicated by "B."

The foreign substance detecting device of the fifth example having the above-described configuration attains effects of enabling overlooking-free, highly-sensitive detection of a minute magnet body, enabling, by color-coded display on the display screen of the display device 3, notification of the presence or non-presence of a package body placed on the table T and foreign substances of a minute magnet body contained therein and display in accordance with the position and orientation of the minute magnet body on the table T, and enabling a package body or a packaged product that is an inspected object to be placed on the table T and inspected without being moved by a conveying means to enable an inspecting device to be simple and compact in configuration and enable detection of a plurality of package bodies simultaneously.

Sixth Example

Figure 27:
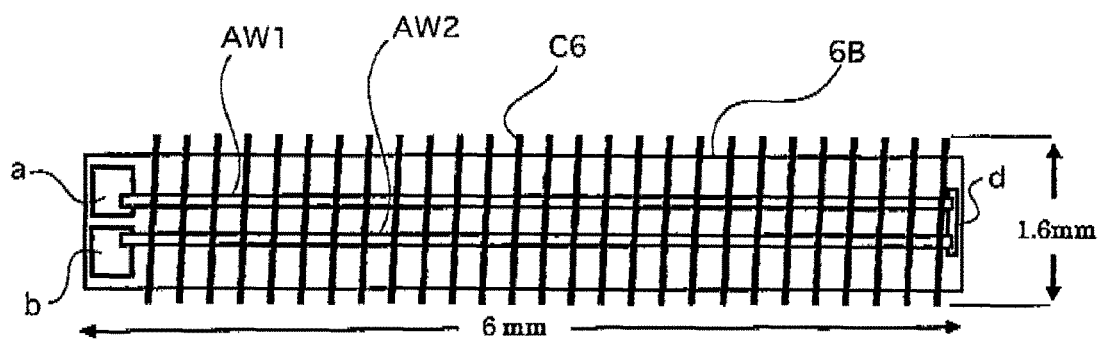
FIG. 27 is a plane view showing an orthogonal (open magnetic circuit type) fluxgate magnetic detecting element of the sixth example.
Figure 28:
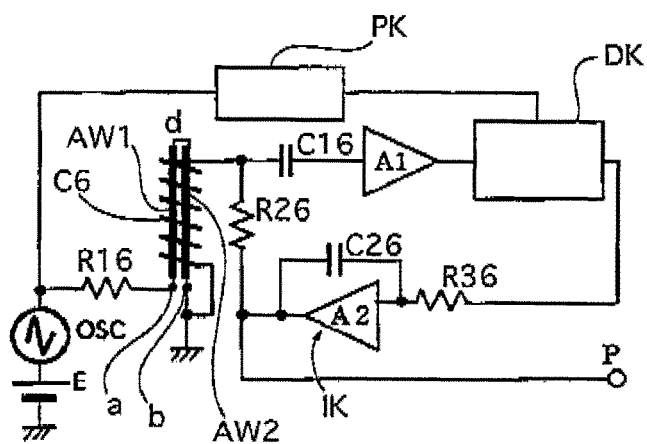
FIG. 28 is a circuit diagram showing a signal processing circuit in the sixth example.

The present invention is applied to a fluxgate magnetic sensor in an open magnetic circuit type fluxgate magnetic sensor of a sixth example that is configured from an orthogonal fluxgate magnetic detecting element, which, as shown in FIG. 27 and FIG. 28, uses amorphous wires as magneto-sensitive bodies and has a detecting coil C6 wound around it.

As an example of the fluxgate magnetic detecting element, the two amorphous wires AW1 and AW2 are disposed in parallel as the magneto-sensitive bodies in a length direction of a ceramic substrate 6B of 6 mm length, the coil C6 is wound on the wires, and a diameter of the coil C6 is 1.6 mm at the maximum.

Two amorphous wires AW3 and AW4 (not shown) that are the same as the two amorphous wires AW1 and AW2 are disposed in a length direction on a second substrate 6B2 (not shown) disposed at a different angle, for example, mutually at a right angle.

The fluxgate magnetic detecting element thus has dimensions of 6 mm length and 1.6 mm maximum diameter and can be manufactured to be of compact size substantially equivalent to that of a magnetic impedance element of the same configuration.

In terms of magnetic circuit, both of the two amorphous wires AW1 and AW2 are of the so-called orthogonal type (open magnetic circuit type) with both ends open to air, and electrodes a and b for electrical connection to the exterior are provided at one end of the amorphous wires AW1 and AW2 that constitute the fluxgate magnetic detecting element, and at another end, the two amorphous wires AW1 and AW2 are electrically connected by an electrode d.

FIG. 28 shows an electrical circuit that constitutes a signal processing circuit thereof and is configured with an oscillation circuit OSC, of a predetermined frequency and voltage, a direct current voltage supply E, with one end connected to the oscillation circuit OSC and another end installed, and a resistor R1 being connected in series to one end of the amorphous wire AW1 via the electrode a to perform a predetermined alternate current excitation and bias excitation.

An alternate current voltage, corresponding to an amplitude of a detected external magnetic field, is output to an output terminal of the detecting coil C6 that is connected to one end of a capacitor C16 and, via another end, to an input terminal of an amplifier A1, and the output that is amplified to a predetermined level by the amplifier Al is configured to be synchronously detected and converted to a voltage corresponding to a magnetic signal by a synchronous detection circuit DK that uses an alternate current voltage of the oscillation circuit OSC, output from a phase control circuit PK, as a reference signal.

The output of the synchronous detection circuit DK is configured such that the output is connected and negatively fed back to the detecting coil C6 via an integrating circuit IK, including an amplifier A2, a resistor R36, connected to the output terminal of the synchronous detection circuit DK and an input terminal of the amplifier A2, and a capacitor C26, connected to the input terminal and an output terminal of the amplifier A2, and through a resistor R26.

Since an offset is thereby eliminated by a null-balance method, operation is performed as a stable fluxgate sensor of satisfactory linearity and as an output, the output of the integrating circuit IK is configured to be obtainable from an output terminal P.

With the orthogonal type (open magnetic circuit type) fluxgate magnetic sensor of the sixth example having the above-described configuration, since alternate current voltages, corresponding to a local magnetic field of a minute magnet body that is detected by two sets (four) of amorphous wires AW1 to AW4 disposed two each on the substrates 6B disposed at different angles, are signal processed by the above-described signal processing circuits and output from the output terminals and since magnetic field components ms are respectively determined, in the same manner as in the example described above, by operating square values by means of square operating elements, then obtaining the sum thereof by an adder, and operating a square root by a square root operating element, an effect of realizing overlooking-free, highly precise detection of the presence or non-presence of a minute magnet body is attained.

When the performance of the open magnetic circuit type fluxgate magnetic sensor of the sixth example was checked by using it in place of the magnetic impedance sensor of the examples described above, it was possible to obtain results (waveforms) similar to those of FIG. 1(b) and FIG. 2(b).

Also, although by omitting the integrating circuit IK and the negative feedback circuit R26 in the sixth example, the output of the synchronous detection circuit PK can be made a magnetic signal output, the manufacturing cost of the electrical circuit can be made low, and zero point drift may become conspicuous in some cases. Although with the sixth example, an example of using the two amorphous wires AW1 and AW2 as the magneto-sensitive bodies in a single fluxgate magnetic sensor was described, reduction to a single amorphous wire may be performed to reduce cost or oppositely, three or more amorphous wires may be used to increase the sensitivity further, and the same also applies to the magnetic impedance sensor described above.

The embodiments and examples described above are taken for explaining. It is to be understood that the present invention should not be restricted by those and any modifications and additions are possible so far as they are not beyond the technical idea of the present invention, which can be understood by the person skilled in the art, based on the descriptions of the patent claims, detailed specification, and Figures.

For example, a minute magnet body detecting sensor, with which at least two magnetic sensors that include magneto-sensitive bodies are used with the respective maximum sensitivity directions being disposed in mutually different directions to measure a predetermined region, may be adopted, a first mode, with which a magnetic field of a minute magnet body that is oriented in an arbitrary direction is detected as components along the plurality of different sensitive axes, may be adopted, detection without dependence on relative signals and orientations of the minute magnet body and the magneto-sensitive bodies of the magnetic sensors and without giving rise to a dead angle is enabled, and minute magnet body detection that is free of omission and highly precise is enabled.

A second mode, with which, in the first mode, mutually adjacent sensors among the plurality of sensors are disposed in states where the maximum sensitivity directions differ by at least 30 degrees or more, may be adopted, and this is practical in that even if an output of one sensor becomes zero when its relative angle θ with respect to a minute magnet body is 90 degrees, another sensor differs in angle by 30 degrees or more and is therefore 60 degrees or less in relative angle θ with respect to the minute magnet body, enabling a detection output of at least approximately one half of the local magnetic field of the minute magnet body to be obtained.

A minute magnet body detecting sensor of a third mode may be adopted where, in the first mode, the maximum sensitivity directions of magnetic sensors that include two magneto-sensitive bodies are disposed in directions such that the angle formed mutually is substantially 90 degrees (in substantially two dimensions), and even if one sensor is of zero output when its relative angle θ with respect to a minute magnet body is 90 degrees, the other sensor differs in angle by 90 degrees and is therefore 0 degrees in relative angle θ with respect to the minute magnet body, enabling 100% of the local magnetic field of the minute magnet body to be detected.

A minute magnet body detection sensor of a fourth mode may be adopted where, in the first mode, the maximum sensitivity directions of magnetic sensors including three magneto-sensitive bodies are disposed in substantially three-dimensional directions with angles formed mutually being substantially 90 degrees and even if a minute magnet body is in an arbitrary orientation in three-dimensional space, three sensitivity axis components in three dimensions can be detected and therefore dead-angle-free magnetic measurement is enabled.

A minute magnet body detecting sensor of a fifth mode may be adopted, with which a magnetic signal is obtained by using and signal processing respective signals of a plurality of respective magneto-sensitive bodies or magnetic sensors together, and this enables minute magnet body detection that is free of omission, highly sensitive, and highly precise.

A magnetic sensor of a sixth mode, having a magnetic core, including an amorphous wire or an amorphous ribbon, as a magneto-sensitive body, may be adopted, and this enables minute magnet body detection that is highly sensitive.

A minute magnet body detecting device of a seventh mode may be adopted where a plurality of magnetic sensors are disposed across a path width of the conveyor path to monitor a region through which a minute magnet body that is a detection object is conveyed and passes, and this enables foreign substance detection of a minute magnet body contained in a conveyed package.

A minute magnet body detecting device of an eighth mode may be adopted where a plurality of magnetic sensors are disposed substantially two-dimensionally to monitor a region in which a minute magnet body that is a detection object is present, and this enables foreign substance detection of a minute magnet body contained in a packaged product placed in the monitored region.

Being an art by which a package body, with a minute magnetic body that is a detection object contained or mixing therein, is monitored, as it is passed through, for example, by a belt conveyor 1B, across an entire width of the belt conveyor 1B, a ninth mode that uses a plurality of magnetic sensor units disposes magnetic sensors, with a plurality of magneto-sensitive bodies disposed in plural directions, across the width of the belt conveyor such that individual detected regions mutually overlap partially to realize an omission-free minute magnetic body detecting device.

Also, on a tenth mode, where a plurality of magnetic sensor units, having a plurality of magneto-sensitive bodies disposed in plural directions, are used and disposed substantially two-dimensionally to monitor a region in which is present a package body, with a minute magnet body that is a detection object contained or mixed therein, a foreign substance detecting device that detects the presence of the minute magnet body in a state where the package body is placed in the monitored region without being moved, can also be realized.

A foreign substance detecting device of an eleventh mode of the present invention includes a magnetic detecting element, which, when an electrical pulse current or an alternate current is applied to a magneto-sensitive body of an amorphous material, outputs a voltage corresponding to a local magnetic field generated by a magnetized minute magnetic body positioned around the magneto-sensitive body, a signal processing device, signal processing the voltage to output an output signal, and a display device, performing display on a display portion based on the output signal of the signal processing device, and is configured such that the magnetic detecting element includes at least two magneto-sensitive bodies, which are disposed on a certain plane such that sensitive axes of maximum sensitivity directions thereof are mutually different directions, a plurality of the magnetic detecting elements are disposed at a distance in a detection region on one plane, and, in case of foreign substances of a magnetized minute magnetic body mixed in an inspected object placed in the detection region, the signal processing device performs signal processing based on the voltage output by the magnetic detecting element that detected the local magnetic field of the minute magnetic body to determine an amplitude (which, for example, in a case where there are two magneto-sensitive bodies, is a component along the plane that contains the magneto-sensitive axes of the two magneto-sensitive bodies and, in a case where three mutually orthogonal magneto-sensitive bodies are used, is a total magnetic force component) of the local magnetic field generated by the minute magnetic body and the display device displays, on the display portion, foreign substances of a minute magnetic body mixed in the inspected object placed in the detection region.

Although with the fifth example described above, an example of executing the adjustment of the division levels by software was described, the present invention is not limited thereto, and a modification that performs a level changing method and a division level adjustment using an analog electrical circuit may be adopted and shall be described below using FIG. 22.

Figure 22:
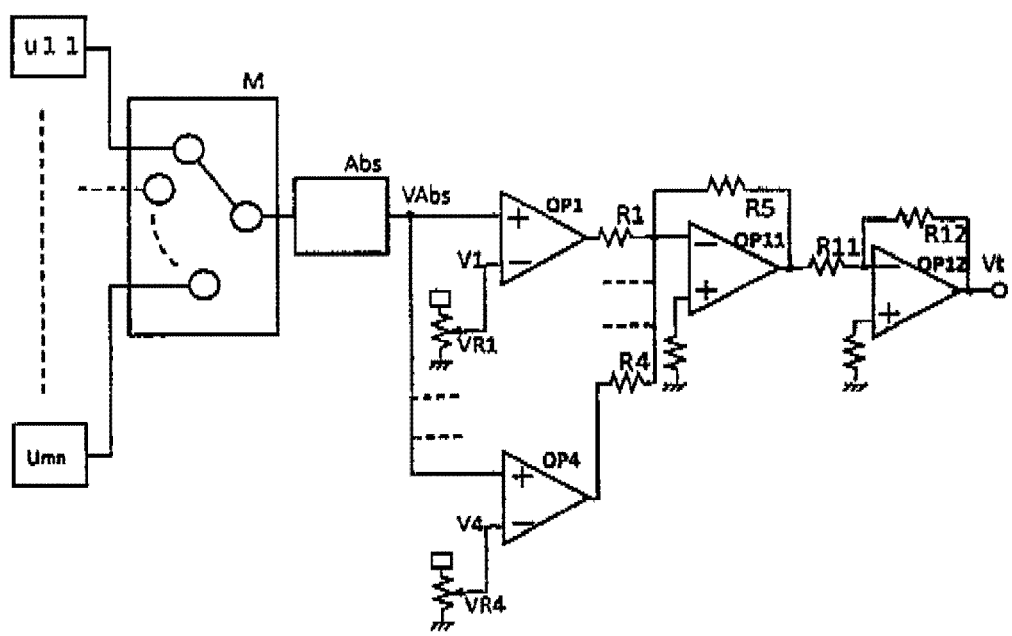
FIG. 22 is a detailed circuit diagram for explaining a modification example, with which the signal processing device in the fifth example is configured by an analog electrical circuit, and adjustment of level classification.

In FIG. 22, magnetic sensor units u11 to umn output analog signal voltages that are detection signals and are transmitted successively to an absolute value circuit Abs by a multiplexer M, which is an analog switch that switches over and transmits analog voltages. A switching timing thereof is, for example, 1 ms. The number of sensor units in the present modification is, for example, 18 units longitudinally and 32 units laterally or 576 units in total and therefore cycling is performed every approximately in 576 ms.

The absolute value circuit Abs is an IC having a function outputting both a positive input voltage and a negative input voltage as a positive voltage. As mentioned above, regardless of whether a detected magnetic field is positive or negative, if the absolute value of its signal is large, it means that the foreign substance is large, and this is accommodated for. The positive signal voltage is thus connected in parallel to positive polarity input terminals of four analog comparators including operational amplifiers OP1 to OP4. Reference voltages set to mutually different predetermined voltages V1 to V4 are respectively input into negative polarity input terminals of the operation amplifiers OP1 to OP4 by sliding electrodes of preset variable resistors VR1 to VR4, which are respectively connected to a power supply and ground.

By the four comparator circuits OP1 to OP4 that are representatively illustrated in FIG. 22, the voltage VAbs, output from the absolute value circuit, is compared with the respective reference voltages V1 to V4 and classified into a level among five stages of 0 volts to V1 volts, V1 to V2 volts, V2 to V3 volts, V3 to V4 volts, and V4 volts or more.

A mode where comparators of a maximum number of, for example, 20, considered in advance to be necessary for use, are connected to an output terminal of the absolute value circuit Abs via switch elements and if, for example, eight of the comparators are to be used, eight of the switch elements are switched on, or a mode where all of the comparators are connected to the absolute value circuit in advance without interposition of the switch elements and if, for example, five of the comparators are to be used, a reference voltage of the five comparator is set and the other comparators are set to a maximum value and prevented from operating may be adopted.

That is, each of the comparator circuits OP1 to OP4 outputs 0 volts if the voltage VAbs, output from the absolute value circuit, is lower than the corresponding reference voltage and outputs a positive voltage of 5 volts if it becomes higher than the corresponding reference voltage.

Respective output terminals of the four comparators are respectively connected to an adding circuit OP11 having input resistors R1 to R4. The input resistors R1 to R4 are all of the same resistance value, for example, of 50 kΩ, and a feedback resistor R5 has a value that is ⅕ that of R1 to R4 and is, for example, 10 kΩ.

Therefore, regardless of from which input terminal of any of the input resistors R1 to R4 a signal is input, an addition coefficient at an output terminal of the adding circuit is -⅕. Here, "-," that is, a minus sign is attached because of connection to a negative polarity input terminal.

Also, a coefficient of a sign inverting circuit, including an OP12 and resistors R11 and R12 connected to an output terminal of the adding circuit OP11, is -1.

Therefore, if the output signal VAbs of the absolute value circuit, that is, the input voltage of the four comparators is lower than the reference voltage V1, the outputs of all comparators are 0 volts and an output Vt of the sign inverting circuit is also 0 volts. If the VAbs exceeds V1 but is lower than V2, just the output of the comparator including the OP1 outputs 5 volts. At this time, 1 volt is output as the voltage Vt of the output terminal of the sign inverting circuit.

And when the VAbs exceeds V4 volts, the outputs of all comparators become 5 volts and therefore the output of the sign inverting circuit becomes 4 volts.

That is, the Vt is 0 volts for the VAbs of 0 volts to V1 volts, 1 volt for V1 to V2 volts, 2 volts for V2 to V3 volts, 3 volts for V3 to V4 volts, and 4 volts for V4 volts or more.

That is, the output of the absolute value circuit, that is, a magnetic signal of the sensor units u11 to umn is classified into a level and output as a signal voltage of any of five stages as the output voltage Vt of the sign inverting circuit. Here, the VR1 to VR4 are preset variable resistors and can be adjusted arbitrarily as necessary.

The output terminal of the sign inverting circuit is connected to an analog input terminal of an unillustrated computer. In correspondence to the input voltage Vt, the computer performs color selection of five stages where 0 volts is black, 1 volt is grey, 2 volts is white, 3 volts is yellow, and 4 volts is red and performs color-coded display in correspondence to the 576 two-dimensional segments.

Also, although the array of the sensor units u11 to umn in the fifth example described above is aligned longitudinally and laterally along straight lines and spaced equidistantly, it is not restricted thereto and a modification where the density of disposition is increased or decreased at portions may also be adopted.

Also, in regard to the signal processing by the external computer, although in the fifth example, the total magnetic signal of each of the respective sensor units is color-coded displayed or variable-density displayed independently one by one, a modification that performs signal processing, such as filtering, averaging, or signal enhancement, etc., with the inclusion of the signals of a plurality of mutually adjacent or close-by sensor units to realize a foreign substance detecting device of higher precision may also be adopted.

Figure 19:
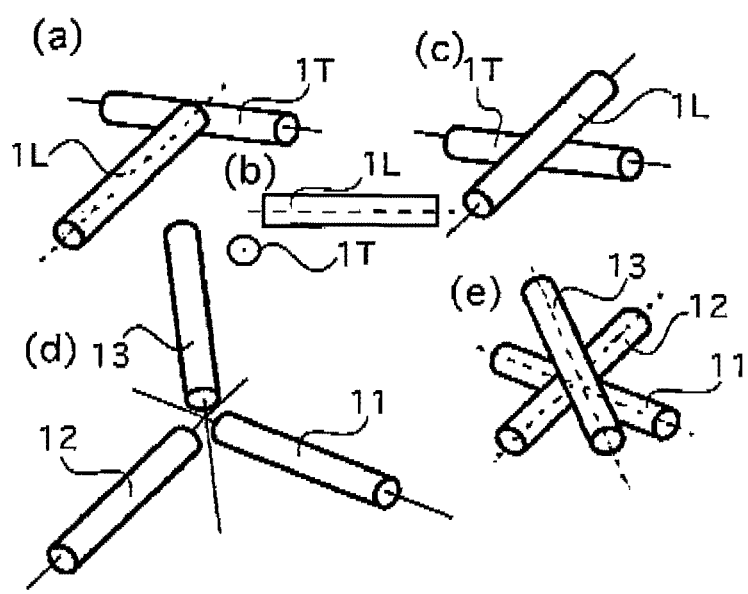
FIGS. 19a, 19b, 19c, 19d and 19e show explanation diagrams for explaining disposition modes of two and three magneto-sensitive bodies.

Although with the above-described fifth example, an example was described where the two magneto-sensitive bodies 11 and 12 are disposed in an L shape, with a fixed distance between one ends thereof, on substantially one plane in a rectangular package of the sensor units u11 to umn, the present invention is not limited thereto, and as shown in FIGS. 19(a) to (c), it is also possible to dispose a lateral rod portion 1T, extending in a lateral direction of a T shape or cross shape, on a horizontal plane that is one of two horizontal planes with a vertical distance inside the package and dispose a longitudinal rod portion 1L, extending in a longitudinal direction, on the other horizontal plane, to dispose the two magneto-sensitive bodies in layers and dispose the magneto-sensitive axis of the magneto-sensitive body 1L or an extended line thereof such as not to contact or collide with the other magneto-sensitive body 1T to enable a magnetic flux and a magnetic field local portion generated by a minute magnetic body and passing through the package to be captured and detected more effectively. A mode may also be adopted where the one magneto-sensitive body 1T that is disposed at the upper side is disposed at an upper surface of the package or a portion close to the upper surface and the other magneto-sensitive body 1L is disposed at a lower surface of the package or a portion close to the lower surface.

A modification may also be adopted where, as shown in FIG. 19(d), by disposing, on one plane in a rectangular or circular package of a sensor unit, three magneto-sensitive bodies 11, 12, and 13 at angular intervals of 120 degrees in a substantially Y shape, maintaining a distance at a central portion at which one ends of the three magneto-sensitive bodies are concentrated, and disposing the magneto-sensitive axis or an extended line thereof of each magneto-sensitive body 11 such as not to contact or collide with another magneto-sensitive body, even if the output of one magneto-sensitive body is 0 or close thereto, detection is enabled based on the outputs of the other two magneto-sensitive bodies and a magnetic flux and a local magnetic field generated by a minute magnetic body and passing through the package can thereby be captured and detected more effectively while effectively avoiding magnetic interference mutually of the magneto-sensitive bodies on one plane.

Further, in FIG. 19(e), three magneto-sensitive bodies, disposed on different horizontal planes in a vertical direction in a rectangular or circular package of a sensor unit, are disposed in layers such as to be at relative angles of 120 degrees mutually to thereby dispose the three magneto-sensitive bodies 11, 12, and 13 in layers in a package of small plane area, and this may be adopted as a modification where with this disposition, a sensor package disposition of short pitch, enabling omission-free detection, is enabled, a magnetic flux and a local magnetic field generated by a minute magnetic body and passing through the package can be captured and detected more effectively while effectively avoiding mutual magnetic interference of the magneto-sensitive bodies, and local magnetic field detection of high sensitivity by three magneto-sensitive bodies is enabled.

Figure 20:
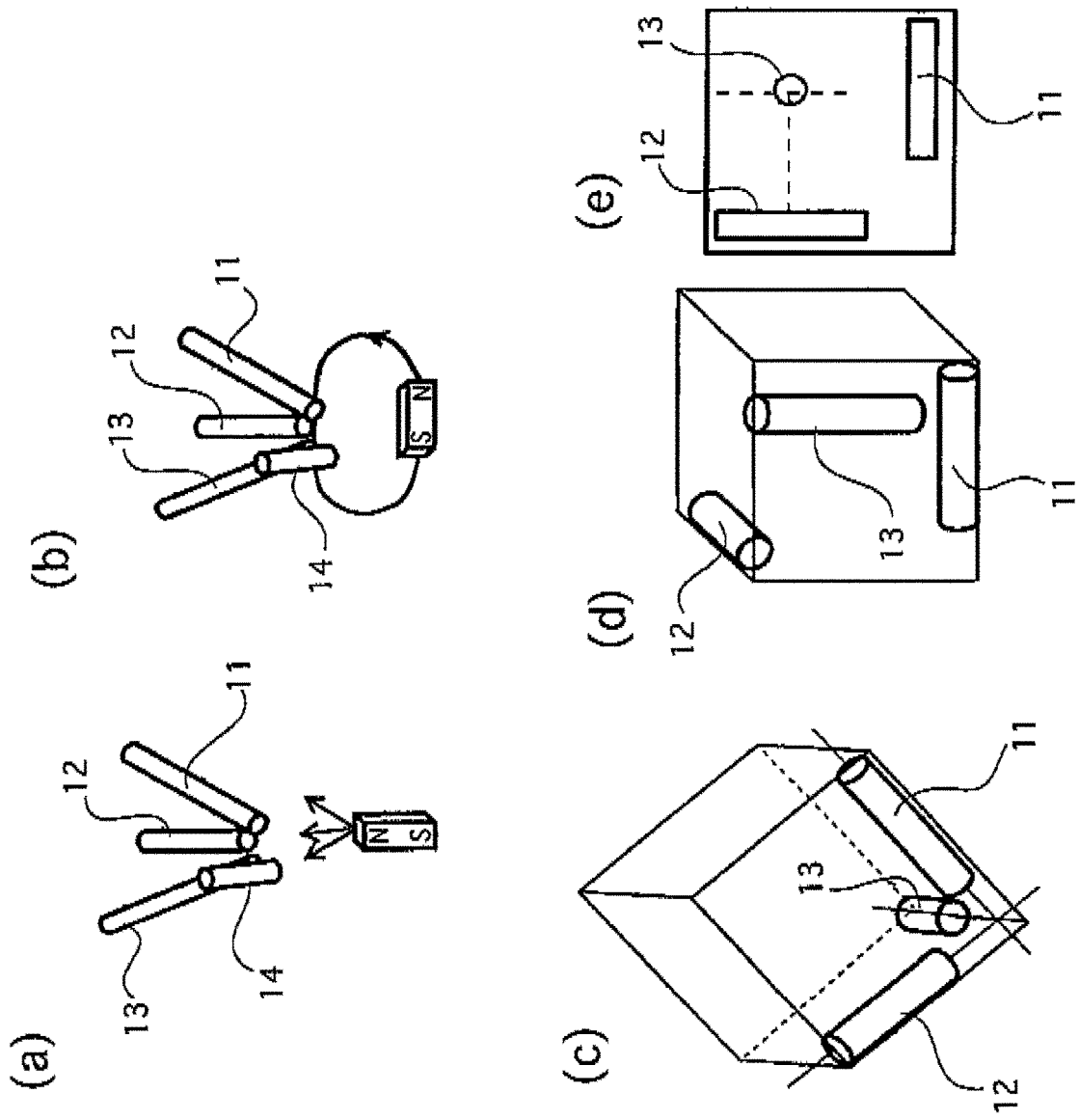
FIGS. 20a, 20b, 20c, 20d, and 20e show explanation diagrams for explaining relationships of magneto-sensitive body disposition modes and sensitivity in a detecting head.

Also, in a case where a direction of a magnetic flux generated by a minute magnetic body is specified, although if, as shown in FIG. 20(a), respective one ends of a plurality of magneto-sensitive bodies 11 to 14 are oriented in a magnetic axis direction in which the magnetic flux is concentrated, the larger the number of the magneto-sensitive bodies 11 to 14, the more signals can be collected (added) and high sensitivity can thus be achieved, in a direction orthogonal to the magnetic axis, that is, if the minute magnetic body and the generated magnetic flux become horizontal as shown in FIG. 20(b), the magnetic flux and the sensitive axes of the magneto-sensitive bodies 11 to 14 become nearly perpendicular and the sensitivity thus decreases. After all, if three magneto-sensitive bodies 11 to 13 are disposed in the three dimensions of the x, y, and z directions as shown in FIGS. 20(c) to (e), the three magneto-sensitive bodies 11-13 detect a magnetic field evenly and can therefore be considered to enable measurement of a total magnetic force thereat or approximately thereof.

Also, although with a three-dimensional disposition of three magneto-sensitive bodies 11 to 13, since measurement of a total magnetic force thereat is enabled and omission in detection of a minute magnetic body is thereby eliminated, with a disposition, where, as shown in FIG. 20(c), the three magneto-sensitive bodies 11 to 13 are disposed along three edge lines connecting to a vertex of a cubic package and one ends of the magneto-sensitive axes and extended lines thereof are concentrically collected at the vertex, the characteristics are the same as described above, and although when a magnetic flux from a minute magnetic body flows from a direction of an extended line of the corner portion, the sensitivity is high as in FIG. 20(a), in a general case where it is not known from which direction a magnetic flux flows, sensitivity of the same trend as a sensor illustrated in FIG. 20(d) and FIG. 20(e), where three magnetic bodies 11 to 13 are disposed along separated edge lines of a cubic package, that is, two magneto-sensitive bodies 11 and 12 are disposed along edge lines that are mutually adjacent across one edge line and the magneto-sensitive body 13 is disposed at an intersection of binormals, drawn from length direction midpoints of the magneto-sensitive bodies 11 and 12, such as to be parallel to an edge line perpendicular to the edge line along which the magneto-sensitive body 11 is disposed, is exhibited.

The sensor illustrated in FIG. 20(d) and FIG. 20(e) is of a mode where, in order to avoid magnetic interference among magneto-sensitive bodies mutually, a magneto-sensitive axis or extended lines thereof of the magneto-sensitive bodies 11 to 13 is separated by a fixed distance such as not to contact or collide with other magneto-sensitive bodies, and by disposing perpendicularly to an intersection in a projection plane of perpendicular lines drawn from the length direction midpoints of the magneto-sensitive bodies 11 and 12, detection of a local magnetic field of a magnetic body by the magneto-sensitive body 13 is enabled even when the local magnetic field of the magnetic body is zero or close thereto by the magneto-sensitive axes 11 and 12.

A magnetic field H oriented in an arbitrary direction at an arbitrary point can be expressed by a synthesis of three directional components of the three dimensional directions x, y, and z, and therefore by using signals Hx, Hy, and Hz, measured by disposing sensitive axes of three magneto-sensitive bodies 11 to 13 of a magnetic head respectively in three directions as shown in FIG. 21(a), and performing the computation shown in FIG. 21(a) mentioned above, the magnetic field H at the location, at which the sensor is placed, can be detected.

That is, as shown in FIG. 21(b), regardless of in which direction a magnetic field H from a minute magnet body is oriented, dead-angle-free magnetic measurement of the local magnetic field of the minute magnetic body is enabled by using the three magneto-sensitive bodies 11, 12, and 13 disposed three-dimensionally in the magnetic head.

Figure 23:
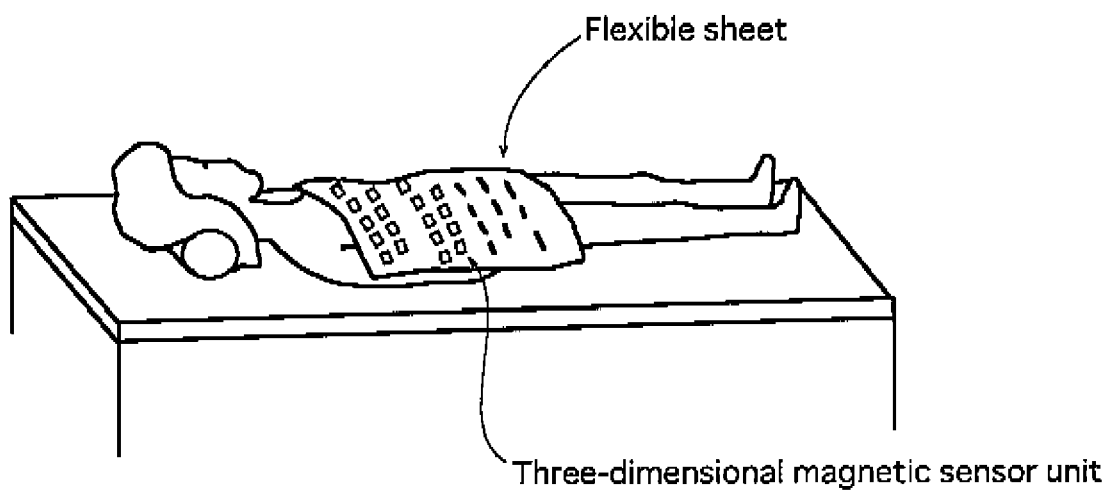
FIG. 23 is an explanation diagram for describing an application example of applying a minute magnetic body detecting sensor of the present invention to biomagnetic measurement.
Figure 24:
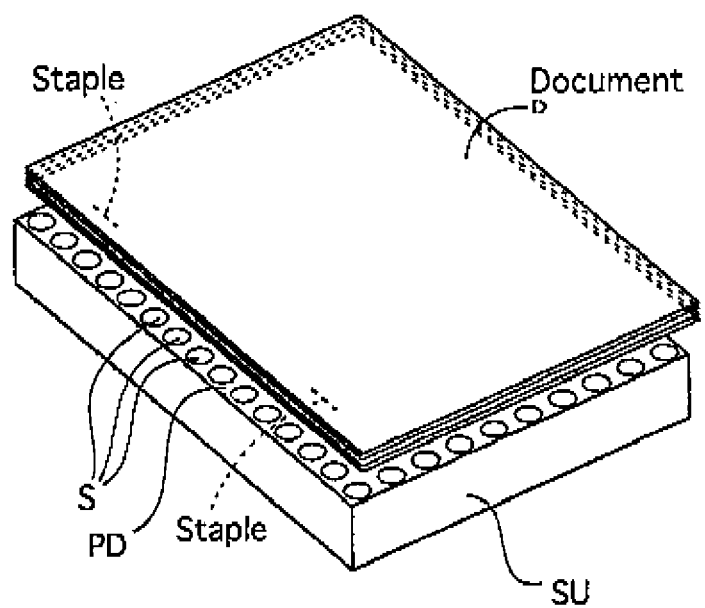
FIG. 24 is a perspective view showing a conventional staple detecting device using fluxgate type magnetic detecting elements.

Although with the foreign substance detecting device described above, an example of performing detection of a minute magnet body, that is, a foreign substance contained in a package body was described, as another application of the present invention, a magnetic sensor for three-dimensional directions may be used as a magnetic sensor unit, and a plurality of these may also be used and disposed two-dimensionally in a flexible sheet, for example, a cloth of natural fibers or a cloth of chemical fibers and, by means of the sheet, coveringly contacted closely, for example, with an upper surface of a human body laid on its back as shown in FIG. 23 to perform biomagnetic measurement of measuring biomagnetic phenomena by measuring a magnetic field generated by an action current generated during muscular contraction or neural activity of the human body or a magnetic field formed by a residual magnetic substance (magnet) taken into the brain or a digestive organ.

A sensor unit may also be contacted closely with a specific portion and/or nonspecific portion that is a portion of a human body without using abovementioned sheet.

Although with the foreign substance detecting device of the fifth example described above, an example of performing color-coding, variable-density display, or contrast display in segments of a grid pattern of a display screen of a display device in correspondence to a foreign substance contained in a package body was described as an example in FIG. 17(b), besides this, a mode may be adopted where, as shown in FIG. c), a plurality of lighting bodies, with which regular top surfaces constitute the display points that are small circles, are disposed on a display screen 30 and by making lighting bodies corresponding to a foreign substance contained in a package be lit in lighting colors in accordance with the characters of "R," "G," and "B," a lit circle of top faces is made large in diameter and lighting by color coding is performed.

Also, although a mode of application to detection of a local magnetic field of a magnet body or a magnetic body made into a magnet was described above, the present invention may also adopt, besides the above, a mode of application to detection of a local magnetic field of a magnetized magnetic body.

Although with the foreign substance detecting device of the fifth example described above, an example of disposing two magneto-sensitive bodies on a substrate and in a package of rectangular shapes was described as an example, besides this, a mode may be adopted where at least two magneto-sensitive bodies are disposed on a substrate and in a package of circular shapes or of polygonal shapes, such as pentagonal shapes, octagonal shapes, etc.

Although in the above description of the examples, description was mostly provided by way of examples using a magnetic impedance element, even when an open magnetic circuit type orthogonal fluxgate type detection element, of which one example was illustrated, is used, miniaturization is possible as with a magnetic impedance element and an extremely highly sensitive magnetic detection performance can be obtained with respect to an axial direction of a magneto-sensitive body, and therefore by disposing at least two magneto-sensitive bodies such that sensitive axes of maximum sensitivity directions are mutually different directions, providing of a minute magnetic body detecting sensor and a foreign substance detecting device that are free of detection omission with respect to foreign substance detection of a minute magnetic body mixed at a state of unspecific orientation can be enabled.

Also, a modification may also be adopted where, as shown in FIG. 25(c), in a closed magnetic circuit type parallel fluxgate type detection element, with exciting coils 10R being respectively wound around vertically extending portions at both sides of a core 10' with which an amorphous wire is formed to an elongate rectangular shape, and a detecting coil 10C' being wound around such as to surround the vertically extending portions, an alternate current is applied to the exciting coils 10R, a voltage, corresponding to a local magnetic field, is detected by the detecting coil, and a signal corresponding to the local magnetic field is output by a signal processing circuit.

INDUSTRIAL APPLICABILITY

The present invention is suitable for such applications as foreign substance detection of a minute magnetic body entering in a packaged product or package body, detection of a minute magnetic body or magnetic ink in a document, detection of iron powder in a film, detection of iron powder in a moving body, application to magnetic pattern measurement, measurement of biomagnetic phenomena, etc.

DESCRIPTION OF SYMBOLS 1 magnetic impedance element
2 signal processing device
3 display device
10, 11, 12, 13 magneto-sensitive body
1B belt conveyor
20 signal processing circuit
21 two square operating element
22 adder
23 square root operating element
24 A/D converter
25 microprocessor
P package

What is claimed is:

1. A minute magnetic body detecting sensor comprising:
a magnetic detecting element for outputting a damped oscillating voltage in response to a local magnetic field generated by a magnetized minute magnetic body such as size 0.1 mm or 0.3 mm, positioned at a state of unspecific position and orientation on which a detection sensitivity is depended around a magneto-sensitive body of an amorphous material to which an electrical pulse current or an alternate current is applied, and
a signal processing device for processing the damped oscillating voltage to output an output signal, wherein
said magnetic detecting element comprises at least two magneto-sensitive bodies which are disposed such that sensitive axes of maximum sensitivity directions thereof are mutually different directions and such that one of said at least two magneto-sensitive bodies is not able to detect the magnetized minute magnetic body and cannot output an output signal of a significant magnitude and another magneto-sensitive body is able to detect the magnetized minute magnetic body and output the output signal of the significant magnitude.

2. The minute magnetic body detecting sensor according to claim 1, wherein
said at least two magneto-sensitive bodies are two-dimensionally disposed.

3. The minute magnetic body detecting sensor according to claim 2, wherein
said two magneto-sensitive bodies, which detect the local magnetic field of the magnetized minute magnetic body, are disposed without contacting in an rectangular relation along end parts of adjacent two sides on a rectangular substrate,
a driver circuit, which is connected to said at least two magneto-sensitive bodies and applies the electrical pulse current or the alternate current, is disposed on said rectangular substrate, and
said signal processing device, which is connected to said at least two magneto-sensitive bodies and which processes the damped oscillating voltage detected by said at least two magneto-sensitive bodies based on the local magnetic field of the magnetized minute magnetic body, is disposed on said rectangular substrate.

4. The minute magnetic body detecting sensor according to claim 1, wherein
at least three magneto-sensitive bodies are three-dimensionally disposed in a space without magnetically interfering.

5. The minute magnetic body detecting sensor according to claim 4, wherein
said three magneto-sensitive bodies which detect the local magnetic field of the magnetized minute magnetic body are disposed in three-dimensional directions such that an angle between mutual sensitive axes thereof is perpendicular, and
said signal processing device connected to said three magneto-sensitive bodies obtains a total magnetic signal component of the local magnetic field generated by the magnetized minute magnetic body based on output signals of said three magneto-sensitive bodies.

6. The minute magnetic body detecting sensor according to claim 1, wherein
said at least two magneto-sensitive bodies are disposed without an extended line of a sensitive axis of one magneto-sensitive body contacting with another magneto-sensitive body, and
at least two detecting coil are wound around said at least two magneto-sensitive bodies and are connected to said signal processing device.

7. The minute magnetic body detecting sensor according to claim 1, wherein
a magnetic impedance element or an orthogonal fluxgate type detection element is adapted as said magnetic detecting element, and
said signal processing device processes output signals based on the damped oscillating voltage of said magnetic detecting element and sums the processed output signals in order to obtain a total magnetic signal component.

8. A foreign substance detecting device comprising:
a magnetic detecting element for outputting a damped oscillating voltage in response to a local magnetic field generated by a magnetized minute magnetic body such as size 0.1 mm or 0.3 mm, positioned at a state of unspecific position and orientation on which a detection sensitivity is depended around a magneto-sensitive body of an amorphous material to which an electrical pulse current or an alternate current is applied,
a signal processing device for processing the damped oscillating voltage to output an output signal, and
a display device for displaying on a display portion based on the output signal of said signal processing device, wherein
said magnetic detecting element comprises at least two magneto-sensitive bodies which are disposed on a plane such that sensitive axes of maximum sensitivity directions thereof are mutually different directions and such that one of said at least two magneto-sensitive bodies is not able to detect the magnetized minute magnetic body and cannot output an output signal of a significant magnitude and another magneto-sensitive body is able to detect the magnetized minute magnetic body and output the output signal of the significant magnitude, and
a plurality of said magnetic detecting elements are disposed with distances in a detection region in the same plane, and wherein
said foreign substance detecting device is configured such that said signal processing device obtains an amplitude of the local magnetic field generated by the magnetized minute magnetic body by processing based on the damped oscillating voltage in response to the local magnetic field of the magnetized minute magnetic body detected by said magnetic detecting element in case of a foreign substance of the magnetized minute magnetic body entering in an inspected object placed on said detection region, and said display device displays the foreign substance of the magnetized minute magnetic body entering in the inspected object placed on said detection region on said display portion.

9. The foreign substance detecting device according to claim 8, wherein
a magnetic impedance element or an orthogonal fluxgate type detection element is adapted as said magnetic detecting element.

* * * * *